United States Patent
Fujino et al.

(10) Patent No.: US 12,060,379 B2
(45) Date of Patent: Aug. 13, 2024

(54) PLASMALOGEN DERIVATIVES

(71) Applicant: Institute of Rheological Functions of Food, Fukuoka (JP)

(72) Inventors: Takehiko Fujino, Fukuoka (JP); Shiro Mawatari, Fukuoka (JP); Toyoharu Yamashita, Fukuoka (JP); Mitsuru Kitamura, Fukuoka (JP); Tatsuo Okauchi, Fukuoka (JP); Shamim Hossain, Fukuoka (JP)

(73) Assignee: Institute of Rheological Functions of Food (JP)

( * ) Notice: Subject to any disclaimer, the term of this patent is extended or adjusted under 35 U.S.C. 154(b) by 800 days.

(21) Appl. No.: 17/050,905

(22) PCT Filed: Apr. 18, 2019

(86) PCT No.: PCT/JP2019/016638
§ 371 (c)(1),
(2) Date: Oct. 27, 2020

(87) PCT Pub. No.: WO2019/208392
PCT Pub. Date: Oct. 31, 2019

(65) Prior Publication Data
US 2021/0238208 A1     Aug. 5, 2021

(30) Foreign Application Priority Data
Apr. 27, 2018  (JP) .................. 2018-086036

(51) Int. Cl.
*C07F 9/10*     (2006.01)
*A61P 25/28*    (2006.01)

(52) U.S. Cl.
CPC .............. *C07F 9/106* (2013.01); *A61P 25/28* (2018.01)

(58) Field of Classification Search
CPC ...................................................... C07F 9/106
See application file for complete search history.

(56) References Cited

U.S. PATENT DOCUMENTS

| | | | |
|---|---|---|---|
| 2006/0105987 A1 | 5/2006 | Miller et al. | |
| 2012/0283223 A1 | 11/2012 | Ifuku et al. | |
| 2018/0327433 A1 | 11/2018 | Fujino et al. | |

FOREIGN PATENT DOCUMENTS

| | | |
|---|---|---|
| DE | 10152376 A1 | 5/2003 |
| EP | 2123281 A1 | 11/2009 |
| JP | 2003012520 A | 1/2003 |
| JP | 2005529969 A | 10/2005 |
| JP | 2006232967 A | 9/2006 |
| JP | 2011136926 A | 7/2011 |
| JP | 5483846 B2 | 5/2014 |
| JP | 2016045112 A | 4/2016 |
| JP | 2016108466 A | 6/2016 |
| JP | 2016111929 A | 6/2016 |
| WO | 1993021191 A1 | 10/1993 |
| WO | 2007061940 A2 | 5/2007 |
| WO | 2010071988 A1 | 7/2010 |
| WO | 2011083827 A1 | 7/2011 |
| WO | 2013037862 A1 | 3/2013 |
| WO | 2013071418 A1 | 5/2013 |

OTHER PUBLICATIONS

Gil-de-Gomez, et al. (Frontiers in Immunology, 2017, 8, 1-11 (abstract), Accession No. 2018:2134194, CAPLUS).*
Otoki, et al. (Lipids, 2017, 52(6), 559-571 (abstract), Accession No. 2017:655453, CAPLUS).*
Yamamoto, et al. (Journal of Experimental Medicine, 2015, 212 (11), 1901-1919 (abstract), Accession No. 2015:1769093, CAPLUS).*
Khan, et al. (WO 2010071988 A1 (abstract), Jul. 1, 2010, Accession No. 2010:819056, CAPLUS).*
Chen, et al. (US 20090131368 A1 (abstract), May 21, 2009, Accession No. 2009:615938, CAPLUS).*
Little, et al. (Prostaglandins, Leukotrienes and Essential Fatty Acids (2007), 77 (3-4), 155-162 (abstract), Accession No. 2007: 1353207, CAPLUS).*
Cook, et al. (WO 2007098585 (abstract), Sep. 7, 2007, Accession No. 2007:998709, CAPLUS).*
Lang, et al. (WO 2005087216 (abstract), Sep. 22, 2005, Accession No. 2005:1021607, CAPLUS).*
Parkinson's disease [online], retrieved from the internet on Jul. 28, 2023, URL: https://www.mayoclinic.org/diseases-conditions/parkinson-disease/symptoms-causes/syc-20376055?p=1.*

(Continued)

*Primary Examiner* — Shawquia Jackson
(74) *Attorney, Agent, or Firm* — Lerner David LLP

(57) ABSTRACT

A compound presented by the general formula (1), its racemic form, or their salt thereof:

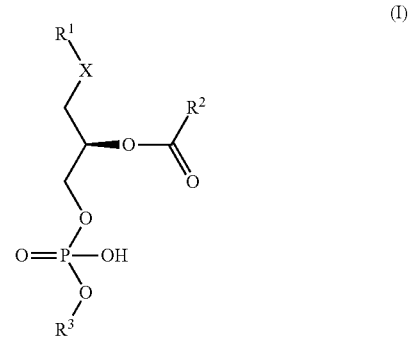

wherein in general formula (1), X represents an oxygen atom, nitrogen atom, sulfur atom, or carbon atom, $R^1$ represents $R^{1a}$—Y—$R^{1b}$, wherein $R^{1a}$ and $R^{1b}$ independently represent a saturated or unsaturated aliphatic hydrocarbon group, aromatic group, heterocyclic group, or a combination thereof, and Y represents an oxygen atom, nitrogen atom, sulfur atom, or carbon atom, $R^2$ independently represents a saturated or unsaturated aliphatic hydrocarbon group, and $R^3$ represents choline, ethanolamine, inositol, or serine.

19 Claims, 7 Drawing Sheets

(56) References Cited

OTHER PUBLICATIONS

Hossain MS, Ifuku M, Take S, Kawamura J, Miake K, Katafuchi T. Plasmalogens rescue neuronal cell death through an activation of AKT and ERK survival signaling. PloS one. Dec. 20, 2013;8(12):e83508.

Hossain MS, Mineno K, Katafuchi T. Neuronal orphan G-protein coupled receptor proteins mediate plasmalogens-induced activation of ERK and Akt signaling. PLoS One. Mar. 2, 2016;11(3):e0150846.

Ifuku M, Katafuchi T, Mawatari S, Noda M, Miake K, Sugiyama M, Fujino T. Anti-inflammatory/anti-amyloidogenic effects of plasmalogens in lipopolysaccharide-induced neuroinflammation in adult mice. Journal of neuroinflammation. Dec. 2012;9(1):1-3.

Guan Z, Wang Y, Cairns NJ, Lantos PL, Dallner G, Sindelar PJ. Decrease and structural modifications of phosphatidylethanolamine plasmalogen in the brain with Alzheimer disease. Journal of neuropathology and experimental neurology. Jul. 1, 1999;58(7):740-7.

Goodenowe DB, Cook LL, Liu J, Lu Y, Jayasinghe DA, Ahiahonu PW, Heath D, Yamazaki Y, Flax J, Krenitsky KF, Sparks DL. Peripheral ethanolamine plasmalogen deficiency: a logical causative factor in Alzheimer's disease and dementia. Journal of lipid research. Nov. 1, 2007;48(11):2485-98.

T. Sanada et al., Serum Plasmalogens in Ischemic Heart Disease, J. Japan Atherosclerosis Society, 11 (3), 535?539, Aug. 1, 1983.

Fujino T, Yamada T, Asada T, Tsuboi Y, Wakana C, Mawatari S, Kono S. Efficacy and blood Plasmalogen changes by Oral Administration of Plasmalogen in patients with mild Alzheimer's disease and mild cognitive impairment: a multicenter, randomized, double-blind, placebo-controlled trial. EBioMedicine. Mar. 1, 2017;17:199-205.

Gregoire L, Smith T, Senanayake V, Mochizuki A, Miville-Godbout E, Goodenowe D, Di Paolo T. Plasmalogen precursor analog treatment reduces levodopa-induced dyskinesias in parkinsonian monkeys. Behavioural Brain Research. Jun. 1, 2015;286:328-37.

Chauveau F, Cho TH, Perez M, Guichardant M, Riou A, Aguettaz P, Picq M, Lagarde M, Berthezene Y, Nighoghossian N, Wiart M. Brain-targeting form of docosahexaenoic acid for experimental stroke treatment: MRI evaluation and anti-oxidant impact. Current neurovascular research. May 1, 2011;8(2):95-102.

Van den Bossche J, Shin J, Thompson DH. Improved plasmalogen synthesis using organobarium intermediates. The Journal of organic chemistry. Jun. 22, 2007;72(13):5005-7.

Rozin AE, Kabanov S, Kupriyanov SE, Serebrennikova GA, Evstigneeva RP. Mass-Spectrometry of Ether Lipids. 2. Mass-Spectrometry of Ether Glycerophospholipids. Bioorganicheskaya Khimiya. Jan. 1, 1977;3(3):397-401.

Li R, Pascal Jr RA. Sulfur-substituted phosphatidylethanolamines. The Journal of Organic Chemistry. Mar. 1993;58(7):1952-4.

Wichmann O, Gelb MH, Schultz C. Probing phospholipase A2 with fluorescent phospholipid substrates. ChemBioChem. Sep. 3, 2007;8(13):1555-69.

International Search Report including Written Opinion for Japanese Application No. 2019016638 mailed May 21, 2019; 7 pages.

Extended European Search Report including Written Opinion for Application No. 19794041.4 dated Feb. 1, 2021, pp. 1-8.

Qin, D. et al., "Synthesis of Plasmalogen via 2,3-Bis-O-(4'-methoxybenzyl)-sn-glycerol," Journal of the American Chemical Society, Jan. 1999, pp. 662-668, vol. 121. XP055766603.

\* cited by examiner

PLASMALOGEN DERIVATIVES

CROSS-REFERENCE TO RELATED APPLICATIONS

This application is a national phase entry under 35 U.S.C. § 371 of International Application No. PCT/JP2019/016638 filed Apr. 18, 2019, which claims the priority from Japanese Patent Application No. 2018-086036 filed Apr. 27, 2018, the entire contents of which are hereby incorporated by reference.

FIELD OF THE INVENTION

The present invention relates to new compounds, more specifically, new compounds equivalent to plasmalogens (plasmalogen derivatives).

BACKGROUND OF THE INVENTION

While phospholipids are important as structural components of a biomembrane, approximately 18% of phospholipids of a mammal biomembrane are plasmalogens that are ether phospholipids. In particular, it is known that many of them are found in brain nerves, heart muscles, skeletal muscles, white blood cells and sperms.

Many of plasmalogens are bound to polyunsaturated fatty acids such as docosahexaenoic acids, arachidonic acids, etc. Therefore, they play not only a role as storage of second messengers for signals between cells such as prostaglandin, leukotriene, etc., but also significant roles as cell fusion, ion transport, etc.

In addition, it has been made clear that plasmalogens themselves involve in signal transmission via a particular G-protein-coupled type receptors (GPCR). For example, while plasmalogens inhibit neuronal cell death by reinforcing activity of protein phosphoenzyme such as AKT, ERK, etc. of a nerve cell (see Non-patent Document 1), it was reported that 5 certain kinds of GPCR involve as a mechanism for such a cell signal transmission (see Non-patent Document 2).

Further, when LPS was injected into an abdominal cavity of a mouse for seven days, IL-1β and TNF-α mRNA expressed strongly in its prefrontal cortex and hippocampus, and β amyloid (Aβ1-16) positive neurons expressed along with activation of glia cells. When plasmalogens were co-administered into the abdominal cavity with the LPS injection, they significantly reduced activation of glia cells involving cytokine production, so did accumulation of As protein. In addition, although the contained amount of plasmalogens was reduced by LPS in the prefrontal area and hippocampus, such a reduction was suppressed by the co-administration of plasmalogens.

In other words, it is considered that plasmalogens have anti-neuroinflammatory and anti-amyloidogenic effects, thereby suggesting their preventive or improvement (therapeutic) application against Alzheimer's disease (see Non-patent Document 3).

It is known that plasmalogens are decreased in patients with brain diseases such as Alzheimer's disease, Parkinson disease, depression and schizophrenia, diabetes, metabolic syndrome, ischemic heart disease, various infectious diseases, and immune disorder.

For example, it was reported in 1999 that in brains of patients with Alzheimer's disease (from dead bodies' brains), ethanolamine-type plasmalogens were quite significantly decreased in its prefrontal cortex and hippocampus (see Non-patent Document 4). In addition, in 2007, it was reported that plasmalogens were decreased in serum of a patient suffering Alzheimer's disease (see Non-patent Document 5).

Further, it was reported that choline-type plasmalogens were decreased in a group of ischemic heart disease as compared to those in a group of normal control (see Non-patent Document 6).

Since it is considered that supplementing those decreased plasmalogens externally can expect preventing and improving effects of those diseases, various attempts have been made conventionally to extract those plasmalogens from an animal tissue. For example in Patent Document 1, it is proposed a method of providing extraction processing to a chicken breast layers using ethanol as extraction solvent to collect an extraction liquid.

In addition, Patent Document 2 proposes a method characterized in providing extraction processing to a bivalve such as scallops using stirred solvent of non-polar organic solvent and branched alcohol, followed by processing with phospholipase A1 (PLA1), to remove foreign substance of diacyl phospholipids by hydrolysis.

In addition, it was reported that a randomized double-blinded clinical trial was carried out to human patients with mild Alzheimer's disease or mild dementia where plasmalogens extracted from the above scallop strips were orally administered, as a consequence of which it strongly suggested that a cognitive function is improved for patients with mild Alzheimer's disease (see Non-patent Document 7).

On the other hand, as a synthesis example of plasmalogen derivant, it is proposed a new plasmalogen precursor that couples α-lipoic acid at a sn-3 position of plasmalogens, for the purpose of preventing or improving various diseases caused from deficient plasmalogens by increasing plasmalogen level (see Patent Document 3). It was reported that such derivant was effective for a monkey model with Parkinson disease (see Non-patent Document 8).

In addition, it is proposed in Patent Document 4 that a derivant with a sn-1 position acetylated is a good carrier of docosahexaenoic acid, which is effective for a mouse model with acute stroke (see Non-patent Document 9).

PRIOR ART DOCUMENTS

Patent Documents

Patent Document 1 Japanese Patent No. 5,483,846
Patent Document 2 Japanese Patent Publication No. 2016-108466
Patent Document 3 WO2010/071988
Patent Document 4 WO2013/037862

Non-Patent Documents

| | |
|---|---|
| Non-patent Document 1 | Md. Shamim Hossain et al, Plasmalogens rescue neuronal cell death through an activation of AKT and ERK survival signaling. PLOS ONE 8 (12): e83508, 2013 |
| Non-patent Document 2 | Md. Shamim Hossain et al, Neuronal Orphan G-Protein Coupled Receptor Proteins Mediate Plasmalogens-Induced Activation of ERK and Akt Signaling. PLoS ONE 11 (3):e0150846, 2016 |

| | | |
|---|---|---|
| Non-patent Document 3 | M. Ifuku et al, Anti-inflammatory/ anti-amyloidogenic effects of plasmalogens in lipopolysaccharide-induced neuroinflammation in adult mice. J of Neuroinflammation, 9:197, 2012 | |
| Non-patent Document 4 | Z. Guan et al, Decrease and Structural Modifications of Phosphatidylethanolamine Plasmalogen in the Brain with Alzheimer Disease, J Neuropathol Exp Neurol, 58 (7), 740-747, 1999 | |
| Non-patent Document 5 | D. B. Goodenowe et al, Peripheral ethanolamine plasmalogen deficiency: a logical causative factor in Alzheimer's disease and dementia, J Lipid Res, 48, 2485-2498, 2007 | |
| Non-patent Document 6 | T. Sanada et al, Serum Plasmalogens in Ischemic Heart Disease, J. Japan Atherosclerosis Society, 11, 535-539, 1983 | |
| Non-patent Document 7 | T. Fujino et al, Efficacy and Blood Plasmalogen Changes by Oral Administration of Plasmalogen in Patients with Mild Alzheimer's Disease and Mild Cognitive Impairment: A Multicenter, Randomized, Double-blind, Placebo-controlled Trial, EBioMedicine, 17: 199-205, 2017 | |
| Non-patent Document 8 | L. Gregoire et al, Plasmalogen precursor analog treatment reduces levodopa-induced dyskinesias in parkinsonian monkeys, Behav Brain Res, 286: 328-337, 2015 | |
| Non-patent Document 9 | C. Fabien et al, Brain-Targeting Form of Docosahexaenoic Acid for Experimental Stroke Treatment: MRI Evaluation and Anti-Oxidant Impact, Current Neurovascular Res, 8 (2): 95-102, 2011 | |
| Non-patent Document 10 | P. Wang et al, Improved Plasmalogen Synthesis Using Organobarium Intermediates, J. Org. Chem, 72: 5005-5007, 2007 | |

SUMMARY OF THE INVENTION

Problem to be Solved by the Invention

Under the above backgrounds, the present invention is to provide new compounds having a heteroatom such as an oxygen atom, nitrogen atom, sulfur atom, etc. at a sn-1 position, which exhibits effects identical to or more than natural plasmalogens.

Solution to the Problem

During the study with respect to plasmalogen derivant, the present inventors designed and synthesized new compounds having a heteroatom such as an oxygen atom, nitrogen atom, sulfur atom, etc. in a carbon chain of a sn-1 position, then performed in-vitro and in-vivo trials. As a consequence, the present inventors found that the new compounds exhibit an effect identical to or more than natural plasmalogens do. The present invention was so completed.

The present design is applicable to any compounds either having a function of plasmalogens by themselves, as a plasmalogen precursor, or as a carrier of docosahexaenoic acids.

The present invention is as follows.

[1] A compound presented by the general formula (1), its racemic form, or their salt:

[Chemical Formula 1]

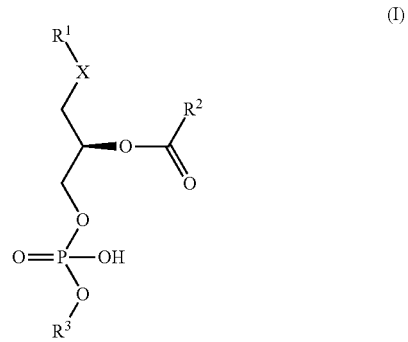

(in the general formula (1), X represents an oxygen atom, nitrogen atom, sulfur atom, or carbon atom, $R^1$ represents $R^{1a}$—Y—$R^{1b}$ (wherein $R^{1a}$ and $R^{1b}$ independently represent a saturated or unsaturated aliphatic hydrocarbon group, aromatic group, heterocyclic group, or a combination thereof, Y represents an oxygen atom, nitrogen atom, sulfur atom, or carbon atom), $R^2$ represents a saturated or unsaturated aliphatic hydrocarbon group, and $R^3$ represents choline, ethanolamine, inositol, or serine.)

[2] The compound, its racemic form, or their salt according to [1], characterized in that X is an oxygen atom.

[3] The compound, its racemic form, or their salt according to [2], characterized in that Y is an oxygen atom, nitrogen atom, or sulfur atom.

[4] The compound, its racemic form, or their salt according to [1], characterized in that X is a nitrogen atom, sulfur atom, or carbon atom.

[5] The compound, its racemic form, or their salt according to [4], characterized in that Y is an oxygen atom, nitrogen atom, sulfur atom, or carbon atom.

[6] The compound, its racemic form, or their salt according to one of [1]-[5], characterized in that $R^{1a}$ and $R^{1b}$ independently represent a saturated or unsaturated aliphatic hydrocarbon group, aromatic group, or a combination thereof.

[7] A pharmaceutical composition characterized in that it contains as an active ingredient the compound, its racemic form, or their salt according to one of [1]-[6].

[8] The pharmaceutical composition according to [7], characterized in that it is used for preventing or improving a disease caused by a reduced level of plasmalogens within a living organism, selected from the group consisting of cranial nerve disease, diabetes, metabolic syndrome, ischemic heart disease, insomnia, infection, and immune disorder.

[9] The pharmaceutical composition according to [8], characterized in that it is used for preventing or improving cranial nerve disease, selected from dementia, Parkinson disease, depression, or schizophrenia.

[10] The pharmaceutical composition according to [9], characterized in that it is used for preventing or improving dementia.

[11] The pharmaceutical composition according to [10], characterized in that dementia is Alzheimer-type dementia.

Effects of the Invention

According to the present invention, new compounds exhibit an effect identical to or more than natural plasmalogens do.

DESCRIPTION OF EMBODIMENTS

Figure 1:
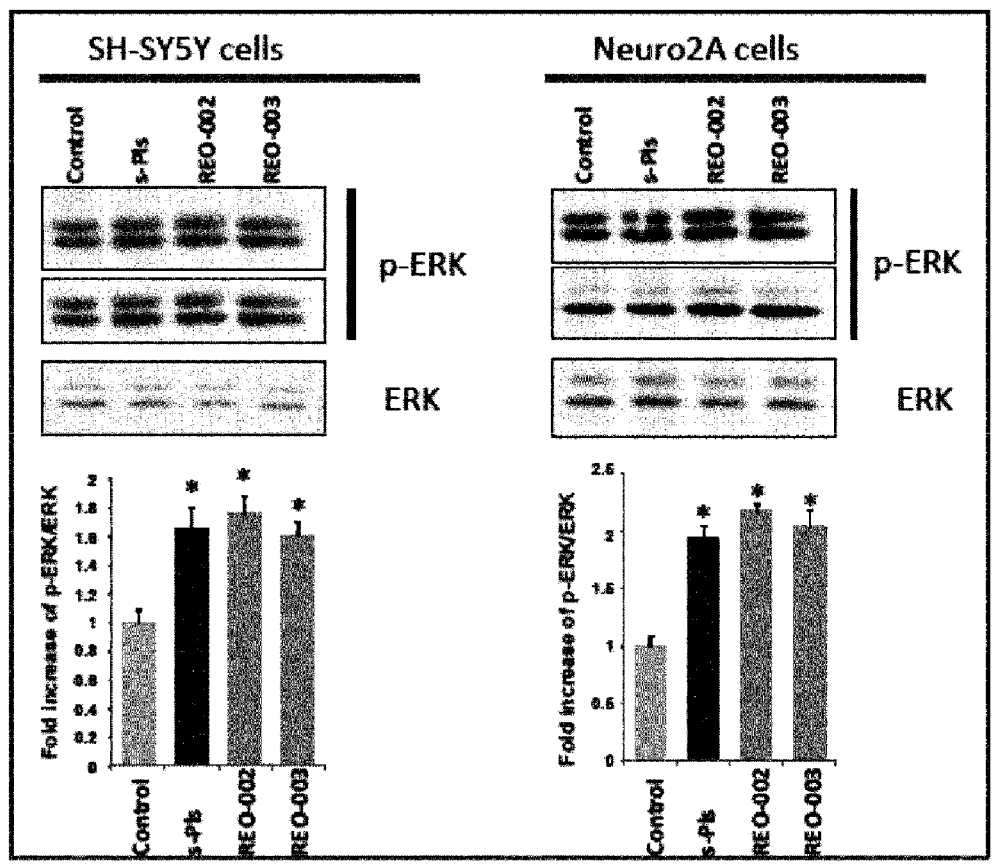
FIG. 1 shows enhanced phosphorylation activities of ERK (ERK1/2) in a neuronal cell line (mouse neuroblastoma derived NEURO2A cell and human neuroblastoma derived SH-SY5Y cell) processed by Compounds (REO-002, REO-003) according to the present invention.

New Compounds According to the Present Invention

New compounds according to the present invention are presented by the following general formula (1), its racemic form, or their salt. In the general formula (1), a carbon atom of a glycerol backbone may have a substituent. The exemplary substituent may be an alkyl group having 1-4 carbon numbers, an alkoxy group having 1-4 carbon numbers, etc.

[Chemical Formula 2]

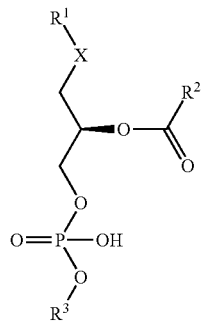

(I)

In the general formula (1), X represents an oxygen atom, nitrogen atom, sulfur atom, or carbon atom, among which it is preferably an oxygen atom or sulfur atom, more preferably an oxygen atom.

$R^1$ represents $R^{1a}$—Y—$R^{1b}$.

Y in $R^1$ represents an oxygen atom, nitrogen atom, sulfur atom, or carbon atom. Where X is an oxygen atom, Y is preferably an oxygen atom, nitrogen atom, or sulfur atom.

$R^{1a}$ and $R^{1b}$ in $R^1$ independently represent a saturated or unsaturated aliphatic hydrocarbon group, aromatic group, heterocyclic group, or a combination thereof, among which it is preferably a saturated or unsaturated hydrocarbon group, aromatic group, or a combination thereof.

An aliphatic hydrocarbon group of $R^{1a}$ and $R^{1b}$ is preferably the one group having 1-30 carbon numbers, more preferably the one having 1-20 carbon numbers, most preferably the one having 1-10 carbon numbers.

In an aromatic group of $R^{1a}$ and $R^{1b}$, an aromatic ring may be monocyclic or condensation polycyclic. Specifically, examples may include a benzene circle, naphthalene ring, anthracene ring, etc., among which a benzene circle is preferred.

In a heterocyclic group of $R^{1a}$ and $R^{1b}$, a hetero ring may comprise, as a ring constituent atom, not only a carbon atom but also a hetero atom, for example 1 to 4 of which, such as a nitrogen atom, sulfur atom, or oxygen atom. It may be monocyclic or condensation polycyclic. Specifically, examples may include a pyrrole ring, furan ring, thiophene ring, imidazole ring, pyrazole ring, oxazole ring, thiazole ring, pyridine ring, pyrazine ring, quinoline ring, indole ring, benzofuran ring, acridine ring, etc.

$R^{1a}$ and $R^{1b}$ may be identical or different each other. In addition, $R^{1a}$ and $R^{1b}$ may have a substituent. The exemplary substituent may be an alkyl group having 1-4 carbon numbers, an alkoxy group having 1-4 carbon numbers.

$R^2$ represents a saturated or unsaturated aliphatic hydrocarbon group, between which an unsaturated aliphatic hydrocarbon group is preferred. A aliphatic hydrocarbon group is preferably the one having 1-50 carbon numbers, more preferably the one having 10-30 carbon numbers, most preferably the one having 15-25 carbon numbers. In addition, $R^2$ may have a substituent. The exemplary substituent may be an alkyl group having 1-4 carbon numbers, an alkoxy group having 1-4 carbon numbers. Specifically, it is preferred that when making $R^2$ to $R^2COOH$, it presents ω-3 fatty acid, ω-6 fatty acid, ω-7 fatty acid, ω-9 fatty acid, or ω-10 fatty acid.

$R^3$ represents choline, ethanolamine, inositol, or serine. They may have a substituent. The exemplary substituent may be an alkyl group having 1-4 carbon numbers, an alkoxy group having 1-4 carbon numbers.

A Method for Producing New Compounds According to the Present Invention

New compounds (where X is an oxygen atom) according to the present invention may be produced by using $R^1OH$ ($R^{1a}$—Y—$R^{1b}OH$) as a starting material.

[Synthesis Method 1]

As a starting material, $R^1OH$ ($R^{1a}$—Y—$R^{1b}OH$) is reacted with (2R)-Glycidyl Tosylate presented by the following formula is reacted. Here, instead of (2R)-Glycidyl Tosylate, Epic hlorohydrin and the like may be used.

[Chemical Formula 3]

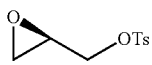

By doing so, the following compound may be obtained (see EXAMPLE 1 Step 1).

[Chemical Formula 4]

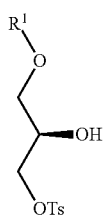

Then the above OH group is protected by a protective group (Z) (see EXAMPLE 1 Step 2).

[Chemical Formula 5]

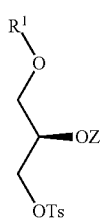

Subsequently, OTs group is replaced by OH group to obtain the following compound (see EXAMPLE 1 Step 3).

[Chemical Formula 6]

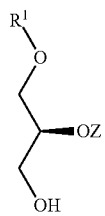

Further, OH group is introduced by a substituent containing a phosphate group and $R^3$ to obtain the following compound (see EXAMPLE 1 Step 4). Here, it is preferred that both phosphate group and $R^3$ are protected by a protective group respectively.

[Chemical Formula 7]

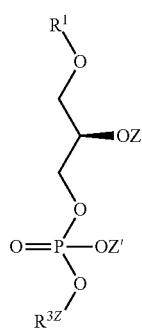

It is followed that deprotection is provided to protective group (Z) to make it to OH group (see EXAMPLE 1 Step 5).

[Chemical Formula 8]

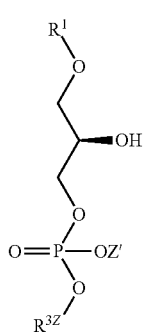

Subsequently, the deprotected OH group is condensed with $R^2CO_2H$ to obtain the following compound (see EXAMPLE 1 Step 6).

[Chemical Formula 9]

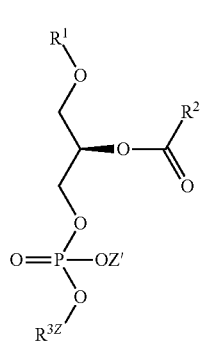

Lastly, protective groups of phosphate group and $R^{3Z}$ are deprotected, and a compound according to the present invention is obtained as presented by the following general formula (I) (see EXAMPLE 1 Step 7).

[Chemical Formula 10]

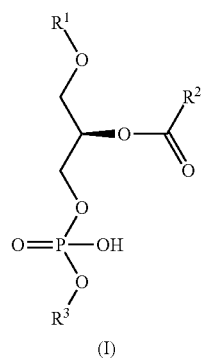

(I)

[Synthesis Method 2]

As a starting material, $R^1OH$ ($R^{1a}$—Y—$R^{1b}OH$) is reacted with TsCl to obtain $R^1OTs$ (see EXAMPLE 3 Step 2). In addition, $R^1OH$ may be obtained by reducing corresponding carboxylic acid ($R^1OOH$) (see EXAMPLE 3 Step 1).

Then, $R^1OTs$ is reacted with (R)-(−)-2,2-Dimethyl-1,3-dioxolane-4-methanol represented by the following formula. Here, a protective group other than acetonide may be used.

[Chemical Formula 11]

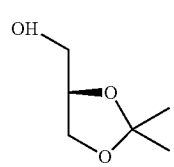

By doing so, the following compound may be obtained (see EXAMPLE 3 Step 3).

[Chemical Formula 12]

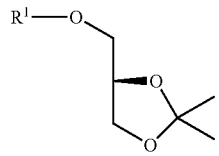

It is followed that deprotection is provided to acetonide of the above compound to obtain the following compound (see EXAMPLE 3 Step 4).

[Chemical Formula 13]

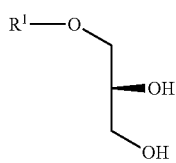

Then, two OH groups are introduced by protective groups (Z, Z') (see EXAMPLE 3 Steps 5, 6).

[Chemical Formula 14]

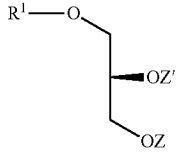

Subsequently, deprotection is provided alternatively to protective group (Z) to make it to OH group (see EXAMPLE 3 Step 7).

[Chemical Formula 15]

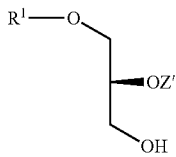

Next, it is introduced by a substituent containing a phosphate group and $R^3$ to obtain the following compound (see EXAMPLE 3 Step 8). Here, it is preferred that both phosphate group and $R^3$ are protected by a protective group respectively.

[Chemical Formula 16]

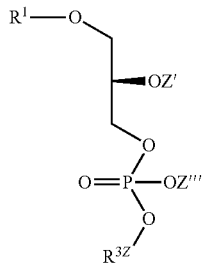

It is followed that deprotection is provided to protective group (Z') to make it to OH group (see EXAMPLE 3 Step 9).

[Chemical Formula 17]

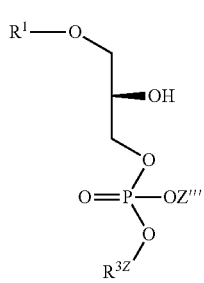

Subsequently, the deprotected OH group is condensed with $R^2CO_2H$ (see EXAMPLE 3 Step 10).

[Chemical Formula 18]

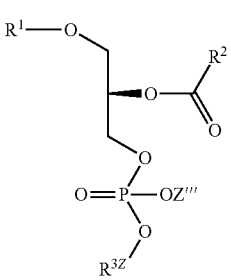

Lastly, protective groups of phosphate group and $R^{3Z}$ are deprotected, and a compound according to the present invention is obtained as presented by the following general formula (I) (see EXAMPLE 3 Step 11).

[Chemical Formula 19]

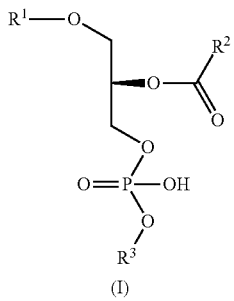

(I)

Pharmaceutical Composition According to the Present Invention

A pharmaceutical composition according to the present invention is characterized in that it contains new compounds according to the present invention presented by the above general formula (I) as an active ingredient, its racemic form, or their salt. The pharmaceutical composition according to the present invention may contain other pharmaceutically acceptable ingredients.

Because new compounds according to the above invention as an active ingredient of a pharmaceutical composition according to the present invention has a structure equivalent to natural plasmalogens, which exhibit an effect identical to or more than plasmalogens do, the pharmaceutical composition achieves an effect identical to or more than plasmalogens do.

A pharmaceutical composition according to the present invention is used for preventing or improving (treating) a disease caused by a decrease of plasmalogen level within a living organism, for example brain diseases such as dementia, Parkinson disease, depression and schizophrenia, diabetes, metabolic syndrome, ischemic heart disease, various infectious diseases, and immune disorder. In particular, it is preferred to be used for preventing or improving (treating) brain diseases such as dementia, Parkinson disease, depression and schizophrenia, among which it is particularly effective for Alzheimer-type dementia.

Example 1

Production was performed for compound REO-004, compound REO-002, compound REO-006 and compound REO-005 according to the present invention presented by the following structural formula (Steps 1-7). The overview of the production process will be described below.

[Chemical Formula 20]

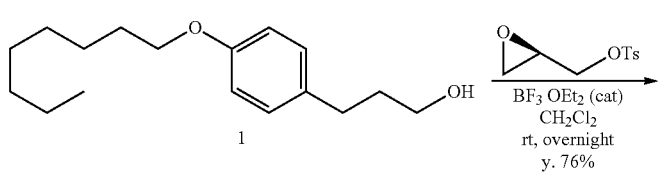

-continued
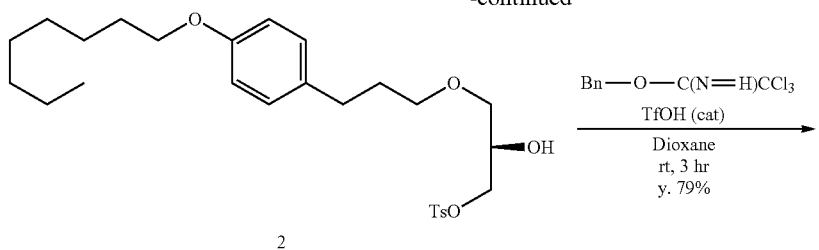
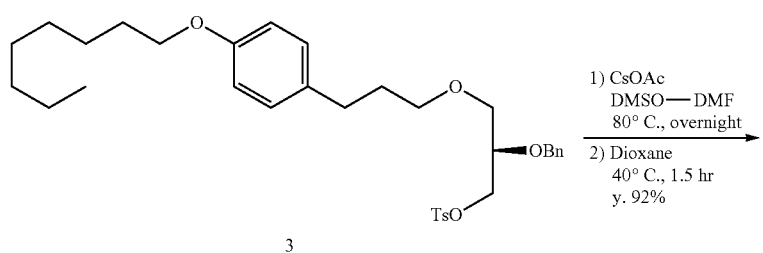
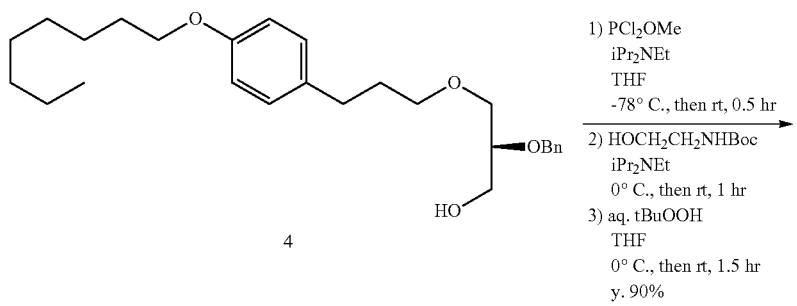
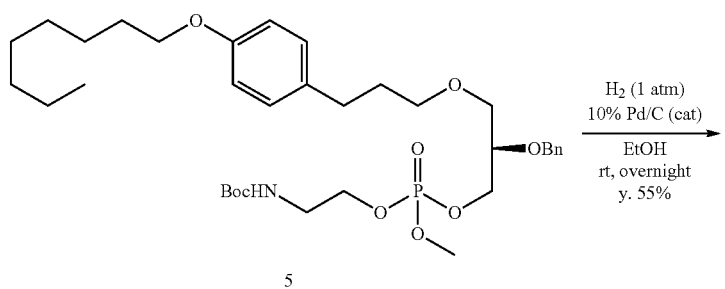
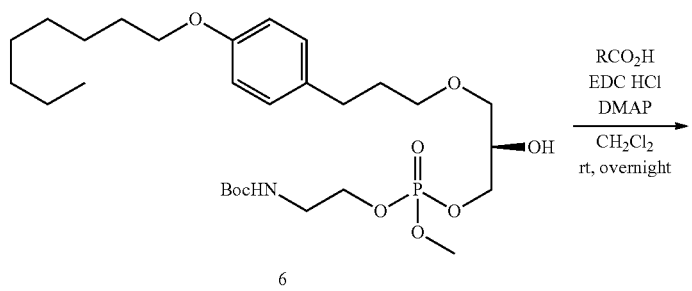

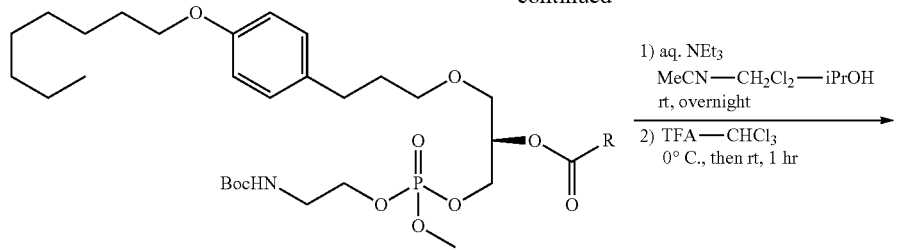

7a RCO₂H: EPA
7b DHA
7c Arachidonic Acid
7d Linoleic Acid

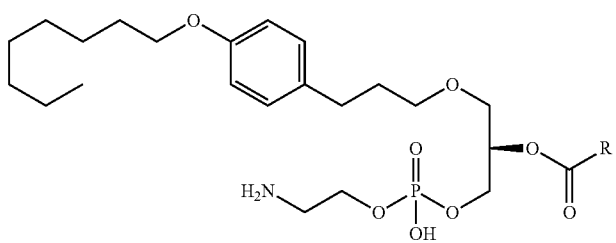

REO-004 RCO₂H: EPA
REO-002 DHA
REO-006 Arachidonic Acid
REO-005 Linoleic Acid

Each step will be described specifically as follows.

[Step 1] Producing compound 2 presented by the following structural formula

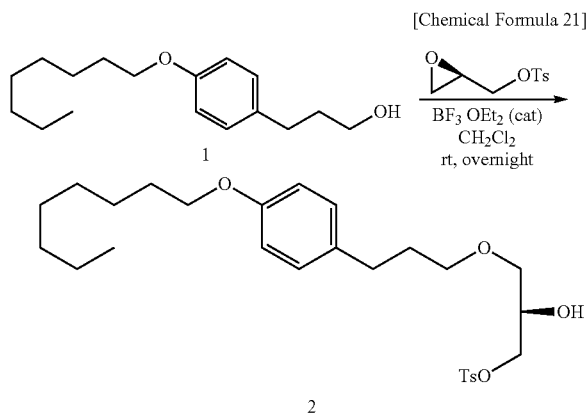

[Chemical Formula 21]

To a stirred solution of compound 1 (5.65 g, 21.1 mmol) and (2R)-Glycidyl Tosylate (5.57 g, 21.1 mmol) in $CH_2Cl_2$ (30 ml) was added $BF_3 \cdot OEt_2$ (0.5 ml, 4 mmol). The solution was stirred at a room temperature overnight under Ar atmosphere. The solvent was evaporated. The residue was purified with Purif-Pack (SI 50, Size 200, AcOEt/hexane: 0-55%) to give compound 2 (7.92 g, y. 76%) as a colorless oil.

Mass EI(+):492

$^1$H NMR (400 MHz, $CDCl_3$): 7.80 (2H, d, J=8.7 Hz), 7.34 (2H, d, J=7.7 Hz), 7.05 (2H, d, J=8.7 Hz), 6.81 (2H, d, J=8.7 Hz), 4.10 (1H, dd, J=10.7, 5.8 Hz), 4.04 (1H, dd, J=10.7, 5.8 Hz), 4.0-3.94 (1H, m), 3.93 (2H, t, J=6.7 Hz), 3.5-3.35 (4H, m), 2.56 (2H, t, J=7.8 Hz), 2.44 (3H, s), 2.36 (1H, d, J=5.8 Hz, OH), 1.9-1.7 (4H, m), 1.5-1.3 (10H, m), 0.89 (3H, t, J=6.8 Hz)

[Step 2] Producing compound 3 presented by the following structural formula.

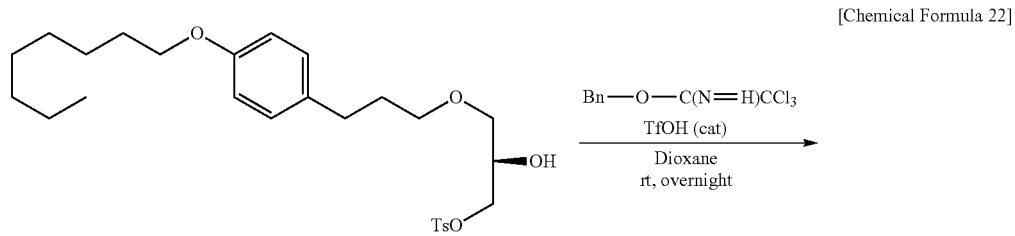

[Chemical Formula 22]

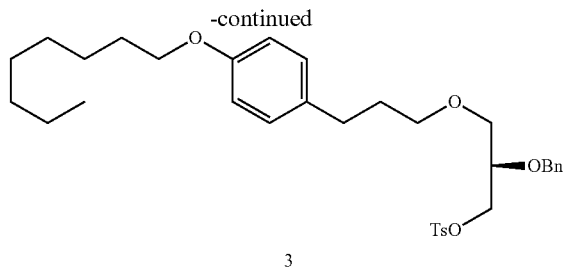

3

To a stirred solution of compound 2 (7.85 g, 16 mmol) and Benzyl Trichloroacetimidate (3.5 ml, 19 mmol) in Dioxane (20 ml) was added Trifluoromethanesulfonic Acid (0.08 ml, 1 mmol). The solution was stirred at a room temperature overnight under Ar atmosphere. The solution was poured into sat.NaHCO₃. The aqueous layer was extracted with CHCl₃ (×2). The extracts were dried over MgSO₄, filtered and evaporated. The residue was purified with Purif-Pack (SI 50, Size 200, AcOEt/hexane: 0-40%) to give compound 3 (7.38 g, y. 79%) as a pale yellow oil.

Mass EI(+):582

$^1$H NMR (400 MHz, CDCl₃): 7.78 (2H, d, J=8.7 Hz), 7.35-7.25 (7H, m), 7.04 (2H, d, J=8.7 Hz), 6.80 (2H, d, J=8.7 Hz), 4.58-4.54 (2H, m), 4.20 (1H, dd, J=10.7, 4.4 Hz), 4.09 (1H, dd, J=10.7, 5.8 Hz), 3.92 (2H, t, J=6.8 Hz), 3.8-3.7 (1H, m), 3.5-3.4 (2H, m), 3.4-3.3 (2H, m), 2.52 (2H, t, J=7.5 Hz), 2.41 (3H, s), 1.8-1.7 (4H, m), 1.5-1.2 (10H, m), 0.88 (3H, t, J=7 Hz)

[Step 3] Producing compound 4 presented by the following structural formula

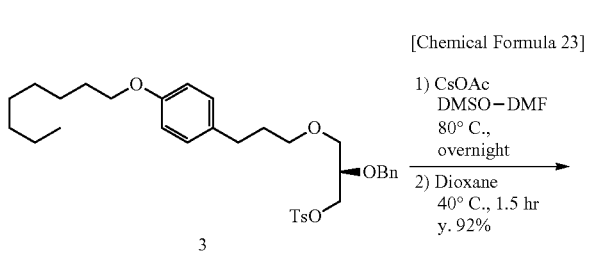

[Chemical Formula 23]

1) CsOAc
DMSO-DMF
80° C.,
overnight
2) Dioxane
40° C., 1.5 hr
y. 92%

4

To a stirred solution of compound 3 (4.4 g, 7.5 mmol) in DMSO (16 ml) and DMF (4 ml) was added CsOAc (2.75 g, 14.3 mmol). The solution was stirred at 80° C. overnight under Ar atmosphere. After cooling, the solution was poured into cold water. The aqueous layer was extracted with AcOEt (×2). The extracts were washed with water (×3), dried over MgSO₄, filtered and evaporated. To the residue was added MeOH (20 ml) and NaOMe (0.27 g, 5 mmol). The mixture was stirred at 40° C. for 1.5 hr under Ar atmosphere. The solvent was evaporated. To the residue was added water and 10% HCl to neutralize. The mixture was extracted with AcOEt (×2). The extracts were dried over MgSO₄, filtered and evaporated. The residue was purified with Purif-Pack (SI 50, Size 60, AcOEt/hexane: 0-45%) to give compound 4 (2.98 g, y. 92%) as a colorless oil.

Mass EI(+):428

$^1$H NMR (400 MHz, CDCl₃): 7.4-7.25 (5H, m), 7.07 (2H, d, J=8.7 Hz), 6.81 (2H, d, J=8.7 Hz), 4.68 (2H, AB, J=11.6 Hz), 4.0-3.88 (2H, m), 3.8-3.4 (7H, m), 2.62 (2H, t, J=7.8 Hz), 2.14 (1H, t, J=8.5 Hz, OH), 1.9-1.7 (4H, m), 1.5-1.2 (10H, m), 0.89 (3H, t, J=7 Hz)

[Step 4] Producing compound 5 presented by the following structural formula

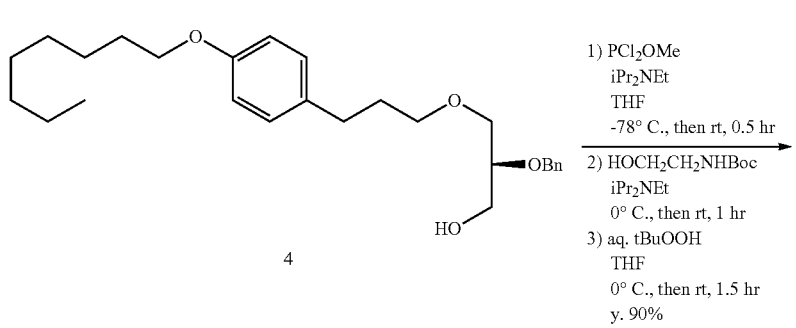

[Chemical Formula 24]

1) PCl₂OMe
iPr₂NEt
THF
-78° C., then rt, 0.5 hr
2) HOCH₂CH₂NHBoc
iPr₂NEt
0° C., then rt, 1 hr
3) aq. tBuOOH
THF
0° C., then rt, 1.5 hr
y. 90%

-continued

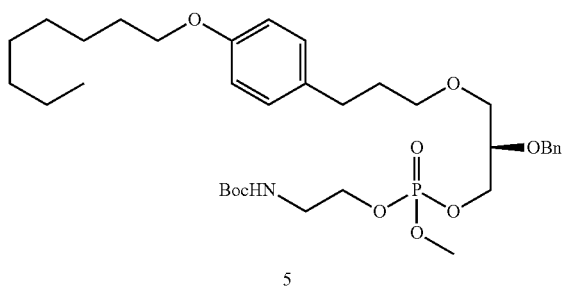

5

To a stirred solution of PCl$_2$OMe (0.58 g, 4.4 mmol) in dry THF (10 ml) was added dropwise a solution of compound 4 (1.71 g, 4 mmol) and iPr$_2$NEt (0.62 g, 4.8 mmol) in dry THF (15 mL) at −78° C. under Ar atmosphere. After the addition, the reaction mixture was stirred for 0.5 hour without the cooling bath. To the reaction mixture was added dropwise a solution of 2-Boc-ethanolamine (0.77 g, 4.8 mmol) and iPr$_2$NEt (0.67 g, 5.2 mmol) in dry THF (15 ml) under ice-cooling. After the addition, the reaction mixture was stirred for 1 hour without the cooling bath. The resultant suspension was filtered off after to the reaction mixture was added AcOEt (30 ml). The filtrate was evaporated. The residue was taken up into THF (15 ml) to which was added tBuOOH (70% aq. solution, 0.9 ml, 6.6 mmol) under ice-cooling under Ar atmosphere. After the addition, the reaction mixture was stirred for 1.5 hour without the cooling bath. The reaction mixture was poured into brine. The aqueous layer was extracted with AcOEt (×2). The extracts were dried over MgSO$_4$, filtered and evaporated. The residue was purified with Purif-Pack (SI 50, Size 120, AcOEt/hexane: 0-80%) to give compound 5 (2.38 g, y. 90%) as a colorless oil.

Mass EI(+):665

$^1$H NMR (400 MHz, CDCl$_3$): 7.4-7.2 (5H, m), 7.07 (2H, d, J=8.7 Hz), 6.81 (2H, d, J=8.2 Hz), 5.1-5.0 (1H, br·s, NH), 4.69 (2H, m), 4.3-4.0 (3H, m), 3.92 (2H, t, J=6.7 Hz), 3.8-3.7 (5H, m), 3.58-3.48 (2H, m), 3.43 (2H, t, J=6.5 Hz), 3.4-3.3 (2H, m), 2.61 (2H, t, J=7.5 Hz), 1.9-1.7 (4H, m), 1.46-1.42 (9H, in), 1.5-1.2 (19H, in), 0.89 (3H, t, J=6.8 Hz)

[Step 5] Producing compound 6 presented by the following structural formula

-continued

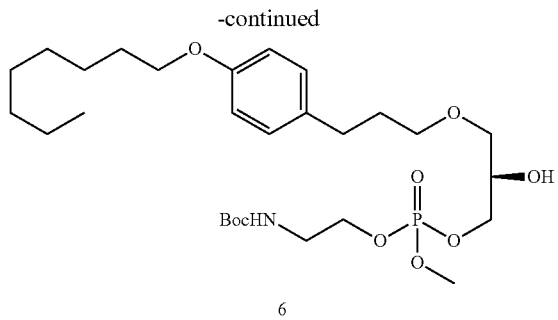

6

To a solution of compound 5 (2.37 g, 4.4 mmol) in Ethanol (30 mL) was added 10% Pd/C (wet, 0.4 g), and the reaction was stirred at a room temperature under H$_2$ atmosphere for 2 days. The catalyst was filtered over Celite. After washing the filter cake with EtOH, the filtrate and washings were evaporated. The residue was purified with Purif-Pack (SI 50, Size 60, AcOEt/hexane: 0-100%) to give compound 6 (1.12 g, y. 55%) as a colorless oil.

Mass FAB(+):576

$^1$H NMR (400 MHz, CDCl$_3$): 7.07 (2H, d, J=8.7 Hz), 6.82 (2H, d, J=8.7 Hz), 5.10 (1H, br. s, NH), 4.2-3.95 (5H, m), 3.95-3.90 (2H, m), 3.80 (3H, d, J=11.6 Hz), 3.5-3.4 (6H, m), 2.97 (1H, d like, OH), 2.61 (2H, t, J=7.7 Hz), 1.9-1.7 (4H, m), 1.45 (9H, s), 1.4-1.2 (10H, m), 0.87 (3H, t, J=7.5 Hz)

[Step 6] Producing compounds 7a-7d presented by the following structural formula

[Chemical Formula 25]

[Chemical Formula 26]

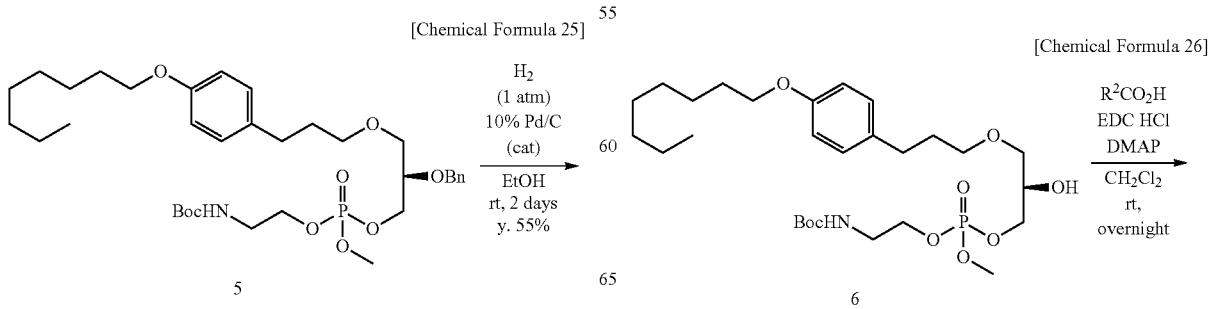

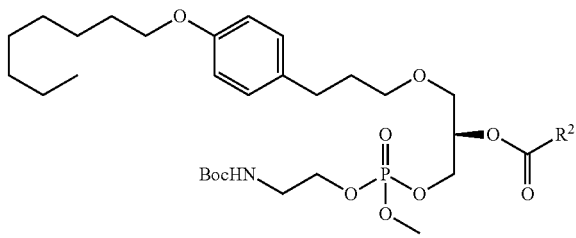

7a RCO$_2$H: EPA
7b DHA
7c Arachidonic Acid
7d Linoleic Acid (Producing Compound 7a)

To a solution of compound 6 (140 mg, 0.24 mmol) in CH$_2$Cl$_2$ (15 ml) was added DMAP (68 mg, 0.56 mmol), EDC. HCl (107 mg, 0.56 mmol) and EPA (100 mg, 0.33 mmol). The reaction was stirred at a room temperature overnight under Ar atmosphere. After evaporating the solvent, to the residue was added AcOEt and water. The layers were separated, and the organic layer was washed with satd. NaHCO$_3$, dried over MgSO$_4$, filtered and evaporated. The residue was purified with Purif-Pack (SI 50, Size 60, AcOEt/hexane: 0-70%) to give compound 7a (174 mg, y. 83%) as a colorless oil.

$^1$H NMR (400 MHz, CDCl$_3$): 7.06 (2H, d, J=7.7 Hz), 6.81 (2H, d, J=7.7 Hz), 5.4-5.3 (10H, m), 5.2-5.0 (2H, m), 4.3-4.15 (2H, m), 4.15-4.0 (2H, m), 3.92 (2H, t, J=6 Hz), 3.77 (3H, dd, J=10.6, 4.8 Hz), 3.6-3.5 (2H, m), 3.5-3.3 (4H, m), 2.9-2.75 (8H, m), 2.59 (2H, t, J=7 Hz), 2.37 (2H, t, J=7.7 Hz), 2.15-2.0 (4H, m), 1.9-1.65 (6H, m), 1.44 (9H, s), 1.4-1.2 (10H, m), 0.97 (3H, t, J=7.7 Hz), 0.88 (3H, t, J=6.8 Hz)

(Producing Compound 7b)

Compound 7b (267 mg, y. 56%) was obtained in a manner equivalent to that compound 7a was produced except that DHA was used instead of EPA.

Mass FAB(+):887

$^1$H NMR (400 MHz, CDCl$_3$): 7.09-7.05 (2H, m), 6.82-6.80 (2H, m), 5.4-5.3 (12H, m), 5.24-5.15 (1H, m), 5.14-5.02 (1H, br. s, NH), 4.3-4.05 (4H, m), 3.92 (2H, t, J=6.7 Hz), 3.82-3.74 (3H, m), 3.6-3.5 (2H, m), 3.5-3.3 (4H, m), 2.9-2.8 (10H, m), 2.63-2.57 (2H, m), 2.41-2.39 (4H, m), 2.12-2.03 (2H, m), 1.9-1.7 (4H, m), 1.44 (9H, s), 1.4-1.2 (10H, m), 0.97 (3H, t, J=7.7 Hz), 0.89 (3H, t, J=6.8 Hz)

(Producing Compound 7c)

Compound 7c (168 mg, y. 84%) was obtained in a manner equivalent to that compound 7a was produced except that Arachidonic Acid was used instead of EPA.

Mass FAB(+):862.6

$^1$H NMR (400 MHz, CDCl$_3$): 7.06 (2H, d, J=8.7 Hz), 6.81 (2H, d, J=8.7 Hz), 5.4-5.3 (8H, m), 5.2-5.0 (2H, m), 4.3-4.15 (2H, m), 4.15-4.05 (2H, m), 3.92 (2H, t, J=6 Hz), 3.77 (3H, dd, 10.6, 4.8 Hz), 3.6-3.5 (2H, m), 3.5-3.3 (4H, m), 2.85-2.75 (6H, m), 2.59 (2H, t, J=7 Hz), 2.37 (2H, t, J=7 Hz), 2.2-2.0 (2H, m), 1.9-1.7 (6H, m), 1.44 (9H, s), 1.4-1.2 (18H, m), 0.88 (6H, m)

(Producing Compound 7d)

Compound 7d (52 mg, y. 26%) was obtained in a manner equivalent to that compound 7a was produced except that Linoleic Acid was used instead of EPA.

Mass FAB(+):838.6

$^1$H NMR (400 MHz, CDCl$_3$): 7.07 (2H, d, J=8.7 Hz), 6.81 (2H, d, J=8.7 Hz), 5.4-5.3 (4H, m), 5.2-5.0 (2H, m), 4.3-4.15 (2H, m), 4.15-4.05 (2H, m), 3.92 (2H, t, J=6.8 Hz), 3.77 (3H, dd, 10.6, 4.8 Hz), 3.6-3.5 (2H, m), 3.5-3.3 (4H, m), 2.77 (2H, t, J=6.8 Hz), 2.59 (2H, t, J=7 Hz), 2.34 (2H, t, J=7 Hz), 2.1-2.0 (4H, m), 1.9-1.7 (4H, m), 1.68-1.58 (2H, m), 1.44 (9H, s), 1.4-1.2 (24H, m), 0.92-0.86 (6H, m)

[Step 7] Producing compound REO-004, compound REO-002, Compound REO-006 and compound REO-005 according to the present invention presented by the following structural formula

[Chemical Formula 27]

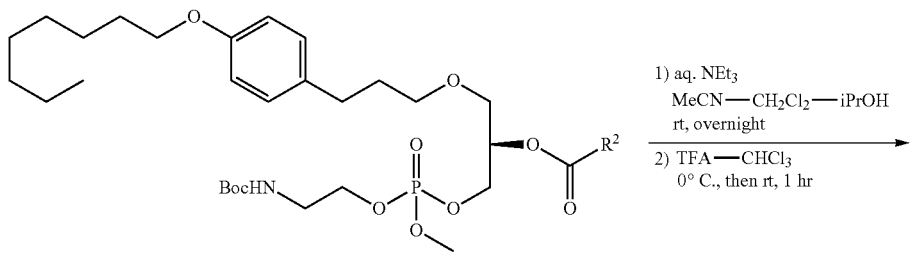

7a RCO$_2$H: EPA
7b DHA
7c Arachidonic Acid
7d Linoleic Acid

-continued

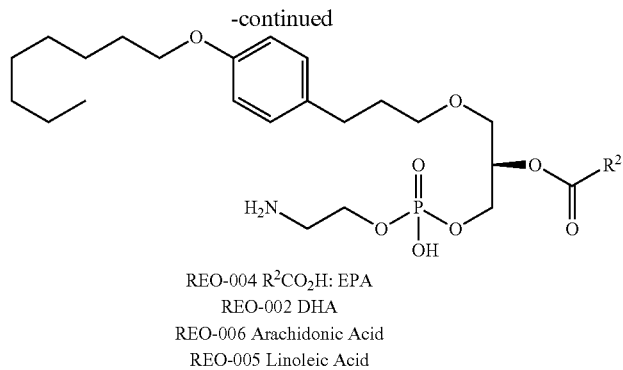

REO-004 R²CO₂H: EPA
REO-002 DHA
REO-006 Arachidonic Acid
REO-005 Linoleic Acid

Producing Compound REO-004 According to the Present Invention

To a solution of compound 7a (170 mg, 0.20 mmol) in $CH_2Cl_2$ (1.5 ml) was added MeCN (3 ml), iPrOH (3 ml) and aq. $NMe_3$ (4.7 ml, 0.33 mmol) followed by stirring overnight at a room temperature under Ar atmosphere. The solvent was evaporated and co-evaporated with toluene to give crude demethylated derivative, to which was added $CHCl_3$ (1.5 ml) and TFA (1.5 ml) under ice-cooling followed by stirring for 1 hour at a room temperature. The solvent was evaporated. The residue was purified with Purif-Pack (SI 50, Size 60, $MeOH/CHCl_3$: 0-30%) to give REO-004 (66.8 mg, y. 45%) as a wet solid.

Mass FAB(+):746.5

$^1$H NMR (400 MHz, $CDCl_3$): 8.45 (3H, br. s), 7.04 (2H, d, J=8.7 Hz), 6.78 (2H, d, J=8.7 Hz), 5.4-5.3 (10H, m), 5.2-5.1 (1H, m), 4.15-3.8 (6H, m), 3.6-3.3 (4H, m), 3.2-3.1 (2H, m), 2.9-2.7 (8H, m), 2.6-2.5 (2H, m), 2.4-2.3 (2H, m), 2.1-2.0 (4H, m), 1.9-1.6 (6H, m), 1.5-1.2 (10H, m), 0.96 (3H, t, J=7 Hz), 0.88 (3H, t, J=6.8 Hz)

Producing Compound REO-002 According to the Present Invention

Compound REO-002 (88 mg, y. 40%) was obtained in a manner equivalent to that compound REO-004 was produced except that compound 7b (265 mg, 0.30 mmol) was used instead of compound 7a (170 mg, 0.20 mmol).

Mass FAB(+):773

$^1$H NMR (400 MHz, $CDCl_3$): 8.35 (3H, br. s), 7.04 (2H, d, J=7.7 Hz), 6.79 (2H, d, J=8.7 Hz), 5.45-5.25 (12H, m), 5.2-5.1 (1H, m), 4.2-3.8 (6H, m), 3.6-3.3 (4H, m), 3.2-3.1 (2H, m), 2.9-2.7 (10H, m), 2.6-2.5 (2H, m), 2.4-2.3 (4H, m), 2.1-1.7 (6H, m), 1.5-1.2 (10H, m), 0.96 (3H, t, J=7.7 Hz), 0.88 (3H, t, J=6.8 Hz)

Producing Compound REO-006 According to the Present Invention

Compound REO-006 (99 mg, y. 69%) was obtained in a manner equivalent to that compound REO-004 was produced except that compound 7c (165 mg, 0.19 mmol) was used instead of compound 7a (170 mg, 0.20 mmol).

Mass FAB(+):748.6

$^1$H NMR (400 MHz, CDCl3): 8.32 (3H, br. s), 7.04 (2H, d, J=8.7 Hz), 6.79 (2H, d, J=8.7 Hz), 5.4-5.3 (8H, m), 5.2-5.1 (1H, m), 4.2-3.8 (6H, m), 3.6-3.3 (4H, m), 3.2-3.1 (2H, m), 2.79 (2H, t, J=6.8 Hz), 2.6-2.5 (2H, m), 2.4-2.3 (2H, m), 2.1-1.6 (8H, m), 1.5-1.2 (18H, m), 0.9-0.8 (6H, m)

Producing Compound REO-005 According to the Present Invention

Compound REO-005 (31 mg, y. 73%) was obtained in a manner equivalent to that compound REO-004 was produced except that compound 7d (49 mg, 0.058 mmol) was used instead of compound 7a (170 mg, 0.20 mmol).

Mass FAB(+):724.6

$^1$H NMR (400 MHz, $CDCl_3$): 8.32 (3H, br. s), 7.04 (2H, d, J=8.7 Hz), 6.79 (2H, d, J=8.7 Hz), 5.4-5.3 (8H, m), 5.2-5.1 (1H, m), 4.2-3.8 (6H, m), 3.6-3.3 (4H, m), 3.2-3.1 (2H, m), 2.79 (2H, t, J=6.8 Hz), 2.6-2.5 (2H, m), 2.4-2.3 (2H, m), 2.1-1.6 (8H, m), 1.5-1.2 (18H, m), 0.9-0.8 (6H, m)

Example 2

Production was performed for compound REO-007 and REO-003 according to the present invention presented by the following structural formula (Steps 1-7). The overview of the production processes will be described below.

[Chemical Formula 28]

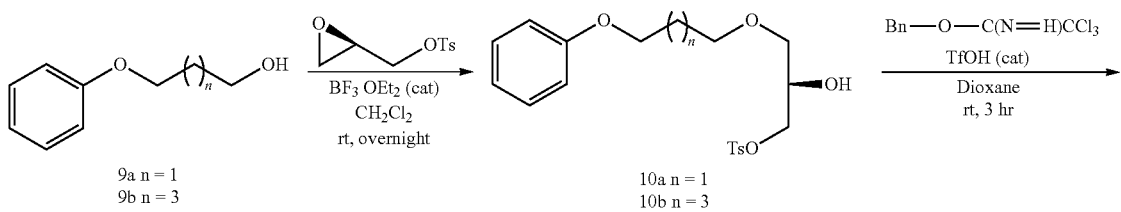

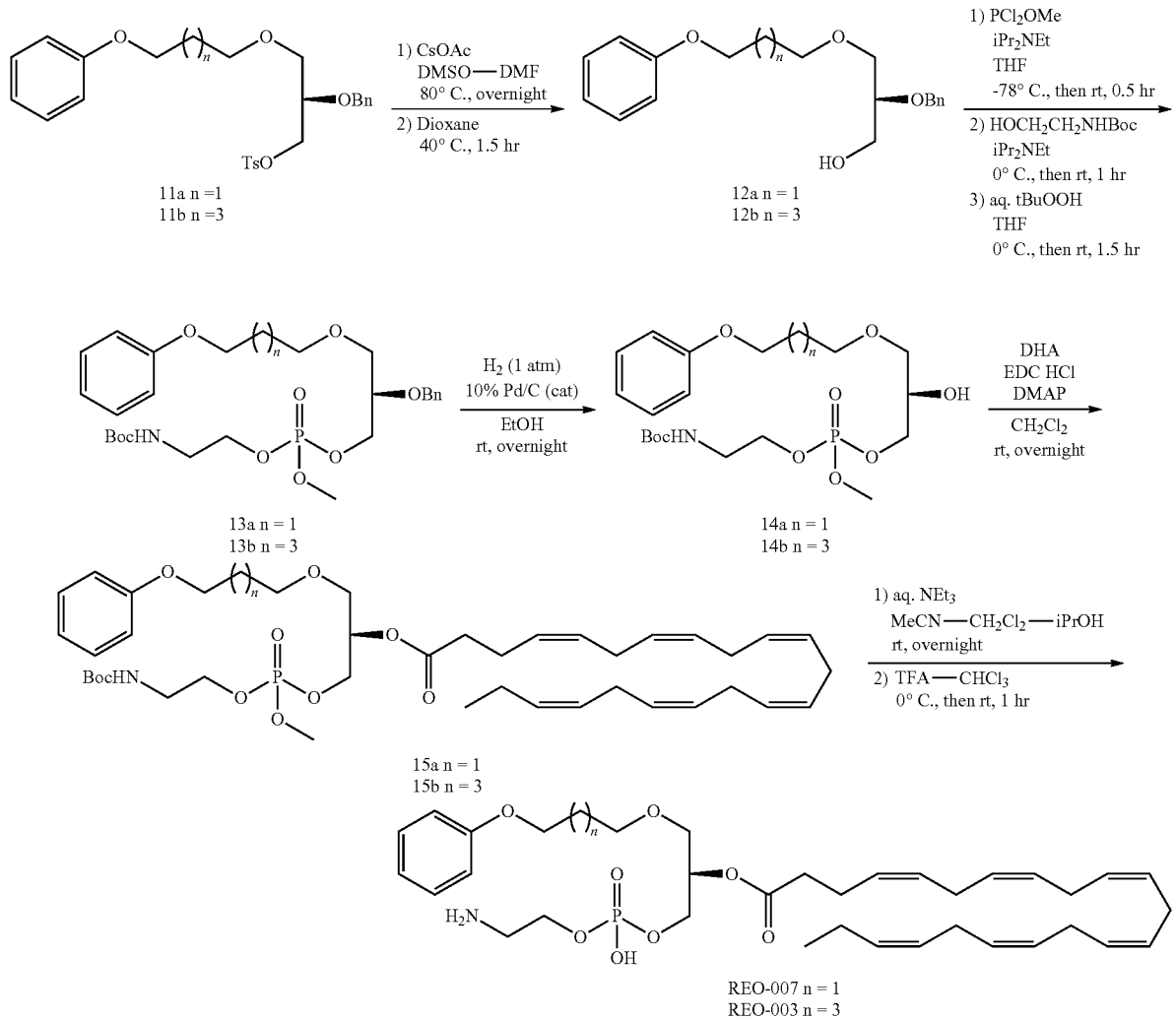

Each step will be described specifically as follows.

[Step 1] Producing compound 10a and 10b presented by the following structural formula

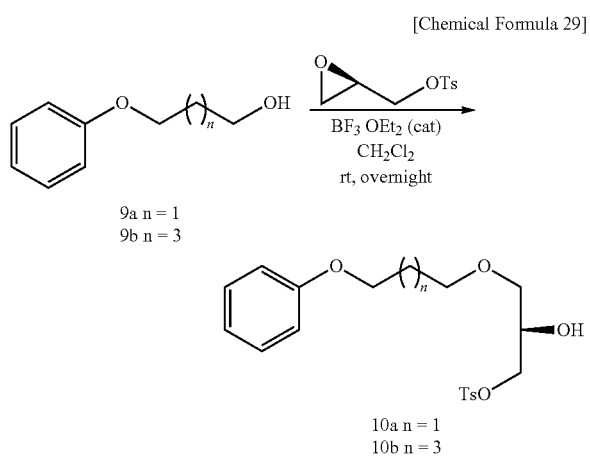

Compound 10a (y. 54%) and compound 10b (y. 62%) were obtained in a manner equivalent to Step 1 of EXAMPLE 1 except that compound 9a and compound 9b were used as a starting material.

(Compound 10a)

Mass EI(+):380

$^1$H NMR (400 MHz, CDCl3): 7.79 (2H, d, J=7.9 Hz), 7.33 (2H, d, J=8.7 Hz), 7.29 (2H, d, J=8.7 Hz), 6.94 (1H, t, J=7.7 Hz), 6.88 (2H, d, J=7.7 Hz), 4.11-3.96 (5H, m), 3.65-3.59 (2H, m), 3.53-3.45 (2H, m), 2.46-2.42 (3H, m), 2.04-1.97 (2H, m)

(Compound 10b)

Mass EI(+):408

$^1$H NMR (400 MHz, CDCl3): 7.79 (2H, d, J=7.8 Hz), 7.34 (2H, d, J=8.7 Hz), 7.29 (2H, d, J=7.7 Hz), 6.93 (1H, t, J=7.7 Hz), 6.89 (2H, d, J=8.7 Hz), 4.09 (1H, dd, 10.6, 4.8 Hz), 4.04 (1H, dd, 10.6, 4.8 Hz), 4.02-3.9 (3H, m), 3.5-3.4 (4H, m), 2.43 (3H, s), 2.39 (1H, d, J=5.8 Hz, OH), 1.79 (2H, q, J=6.8 Hz), 1.7-1.4 (4H, m)

[Step 2] Producing compound 11a and 11b presented by the following structural formula

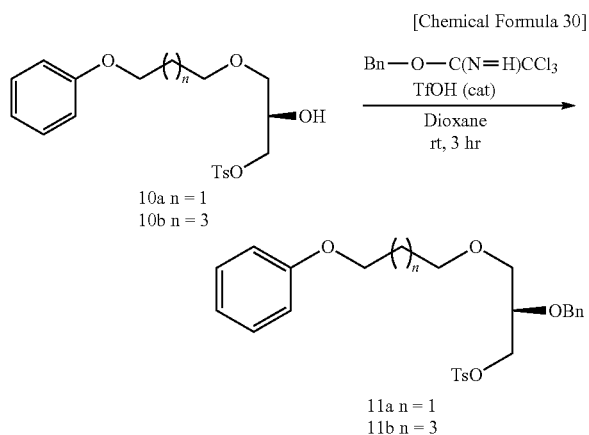

Compound 11a (y. 55%) and compound 11b (y. 57%) were obtained in a manner similar to Step 2 of EXAMPLE 1.

(Compound 11a)

Mass EI(+):470

$^1$H NMR (400 MHz, CDCl3): 7.76 (2H, d, J=7.7 Hz), 7.3-7.2 (9H, m), 6.94 (1H, t, J=7 Hz), 6.88 (2H, d, J=7.7 Hz), 4.56-4.54 (2H, m), 4.2-3.9 (3H, m), 3.8-3.7 (1H, m), 3.56 (2H, t, J=6.7 Hz), 3.5-3.44 (2H, m), 2.42 (3H, s), 2.02-1.93 (2H, m)

(Compound 11b)

Mass EI(+):498

$^1$H NMR (400 MHz, CDCl3): 7.77 (2H, d, J=7.7 Hz), 7.3-6.8 (12H, m), 4.6-4.55 (2H, m), 4.19 (1H, dd, J=10.2, 3.9 Hz), 4.08 (1H, dd, J=10.7, 5.8 Hz), 4.0-3.9 (2H, m), 3.8-3.7 (1H, m), 3.5-3.3 (4H, m), 2.45-2.40 (3H, m), 1.8-1.7 (2H, m), 1.6-1.4 (4H, m)

[Step 3] Producing compound 12a and 12b presented by the following structural formula

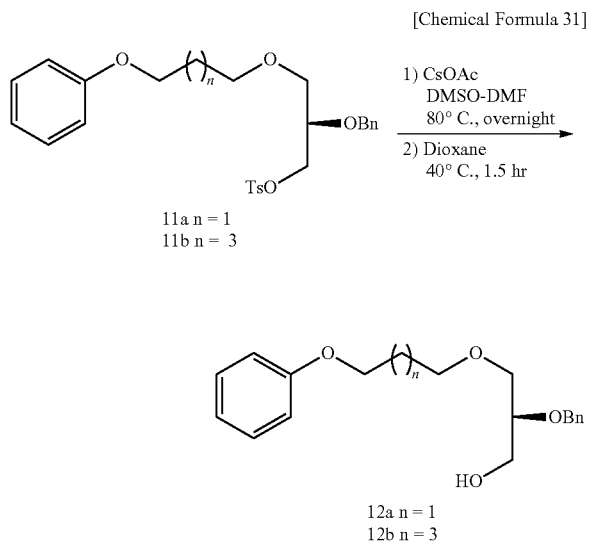

Compound 12a (y. 85%) and compound 12b (y. 88%) were obtained in a manner similar to Step 3 of EXAMPLE 1.

(Compound 12a)

Mass EI(+):316

$^1$H NMR (400 MHz, CDCl3): 7.37-7.26 (7H, m), 6.94 (1H, t, J=7 Hz), 6.89 (2H, d, J=8.7 Hz), 4.64 (2H, AB, J=11.6 Hz), 4.1-4.0 (2H, m), 3.8-3.4 (7H, m), 2.1-2.0 (2H, m)

(Compound 12b)

Mass EI(+):344

$^1$H NMR (400 MHz, CDCl3): 7.4-6.8 (10H, m), 4.66 (2H, AB, J=11.6 Hz), 4.0-3.8 (3H, m), 3.8-3.4 (6H, m), 1.8-1.4 (6H, m)

[Step 4] Producing compound 13a and compound 13b presented by the following structural formula

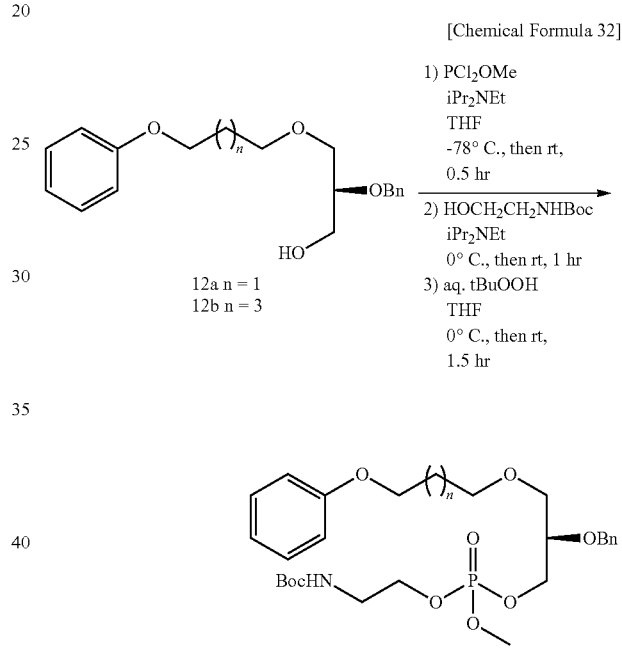

Compound 13a (y. 54%) and compound 13b (y. 76%) were obtained in a manner similar to Step 4 of EXAMPLE 1.

(Compound 13a)

Mass EI(+):553

$^1$H NMR (400 MHz, CDCl3): 7.35-7.25 (10H, m), 6.93 (1H, t, J=7 Hz), 6.89 (2H, d, J=7.7 Hz), 5.1-5.0 (1H, br. s, NH), 4.7-4.6 (2H, m), 4.3-4.0 (6H, m), 3.8-3.5 (8H, m), 3.4-3.3 (2H, m), 2.05-2.0 (2H, m), 1.43 (9H, s)

(Compound 13b)

Mass FAB(+):582

$^1$H NMR (400 MHz, CDCl3): 7.4-6.8 (10H, m), 5.1-4.9 (1H, br. s, NH), 4.7-4.65 (2H, m), 4.3-4.0 (3H, m), 4.0-3.85 (2H, m), 3.8-3.7 (5H, m), 3.6-3.3 (6H, m), 1.8-1.5 (6H, m), 1.44 (9H, s)

[Step 5] Producing compound 14a and 14b presented by the following structural formula

[Chemical Formula 33]

13a n = 1
13b n = 3

→ H₂ (1 atm), 10% Pd/C (cat), EtOH, rt, overnight →

14a n = 1
14b n = 3

Compound 14a (y. 29%) and compound 14b (y. 58%) were obtained in a manner similar to Step 5 of EXAMPLE 1.

(Compound 14a)

Mass EI(+):463

$^1$H NMR (400 MHz, CDCl3): 7.29 (2H, d, J=8.7 Hz), 6.94 (1H, t, J=7 Hz), 6.90 (2H, d, J=7.7 Hz), 5.15-5.05 (1H, br. s, NH), 4.2-4.0 (7H, m), 3.8-3.6 (3H, m), 3.67 (2H, t, J=6 Hz), 3.55-3.5 (2H, m), 3.45-3.35 (2H, m), 3.01 (1H, br. s, OH), 2.06 (2H, q, 5.8 Hz), 1.44 (9H, s)

(Compound 14b)

Mass EI(+):491

$^1$H NMR (400 MHz, CDCl3): 7.2-6.8 (5H, m), 5.10 (1H, br. s, NH), 4.2-3.9 (7H, m), 3.79 (3H, dd, 11.5, 3.8 Hz), 3.5-3.35 (6H, m), 1.8-1.5 (6H, m), 1.44 (9H, s)

[Step 6] Producing compound 15a and 15b presented by the following structural formula

[Chemical Formula 34]

14a n = 1
14b n = 3

→ DHA, EDC HCl, DMAP, CH₂Cl₂, rt, overnight →

15a n = 1
15b n = 3

Compound 15a (y. 76%) and compound 15b (y. 65%) were obtained in a manner similar to Step 6 of EXAMPLE 1.
(Compound 15a)
Mass FAB(+):774.5
¹H NMR (400 MHz, CDCl3): 7.3-7.2 (2H, m), 7.0-6.8 (3H, m), 5.5-5.3 (12H, m), 5.2-5.0 (2H, m), 4.2-4.0 (6H, m), 3.8-3.7 (3H, m), 3.7-3.5 (4H, m), 3.4-3.3 (2H, m), 2.9-2.8 (8H, m), 2.5-2.3 (6H, m), 2.1-2.0 (4H, m), 1.44 (9H, s), 0.97 (3H, t, J=7 Hz)

(Compound 15b)
¹H NMR (400 MHz, CDCl$_3$): 7.2-6.8 (5H, m), 5.4-5.3 (12H, m), 5.2-5.0 (2H, m), 4.2-4.0 (4H, m), 4.0-3.9 (3H, m), 3.8-3.7 (2H, m), 3.6-3.3 (6H, m), 2.9-2.8 (10H, m), 2.41 (4H, m), 2.1-2.0 (2H, m), 1.8-1.7 (2H, m), 1.7-1.4 (4H, m), 1.44 (9H, s), 0.97 (3H, t, J=7.7 Hz)

[Step 7] Producing compound REO-007 and REO-003 presented by the following structural formula

[Chemical Formula 35]

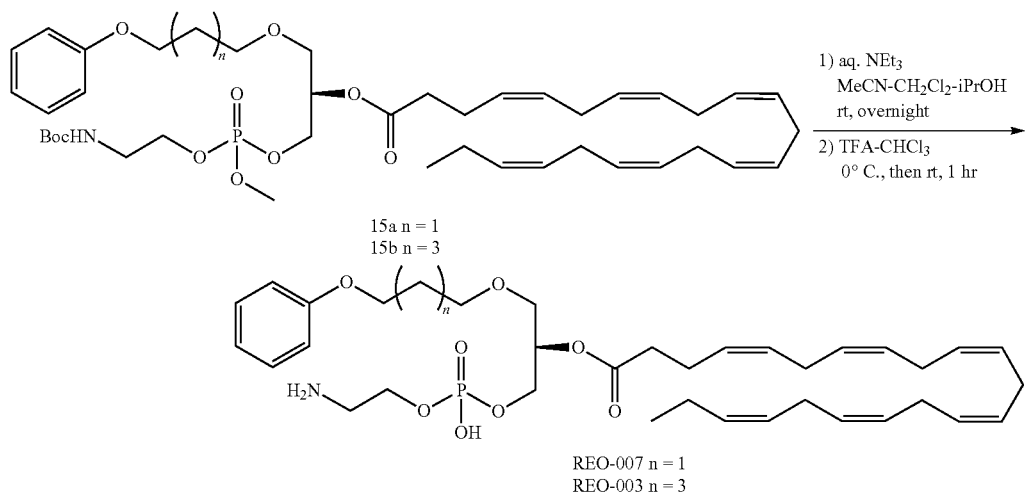

Compound REO-007 (y. 80%) and compound REO-003 (y. 42%) were obtained in a manner similar to Step 7 of EXAMPLE 1.
(Compound REO-007)
Mass FAB(+):660.4
¹H NMR (400 MHz, CDCl3): 8.30 (3H, br. s), 7.3-7.2 (2H, m), 6.95-6.85 (3H, m), 5.4-5.3 (12H, m), 5.2-5.1 (1H, m), 4.1-3.9 (6H, m), 3.7-3.5 (4H, m), 3.2-3.0 (2H, m), 2.9-2.7 (10H, m), 2.4-2.3 (4H, m), 2.2-1.9 (4H, m), 0.97 (3H, t, J=7 Hz)
(Compound REO-003)
Mass FAB(+):688
¹H NMR (400 MHz, CDCl3): 8.42 (3H, br. s), 7.2-6.8 (5H, m), 5.4-5.3 (12H, m), 5.2-5.1 (1H, m), 4.1-3.8 (6H, m), 3.6-3.3 (4H, m), 3.2-3.1 (2H, m), 2.9-2.8 (10H, m), 2.4-2.3 (4H, m), 2.1-2.0 (2H, m), 2.0-1.7 (2H, m), 1.7-1.3 (4H, m), 0.96 (3H, t, J=7.7 Hz)

Example 3

Production was performed for compound KIT-007 according to the present invention presented by the following structural formula (Steps 1-11). The overview of the production processes will be described below.

[Chemical Formula 36]

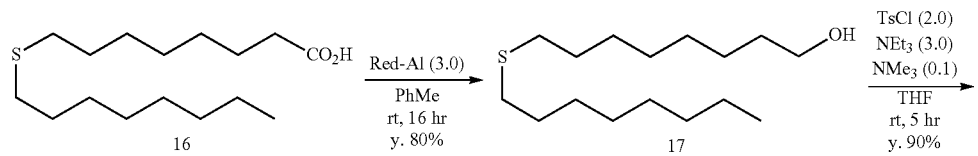

-continued
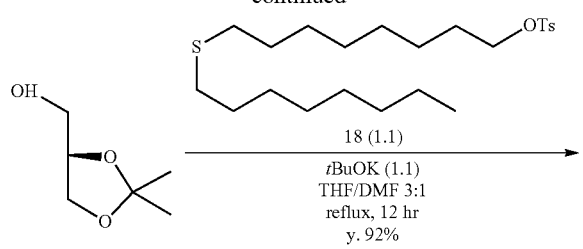
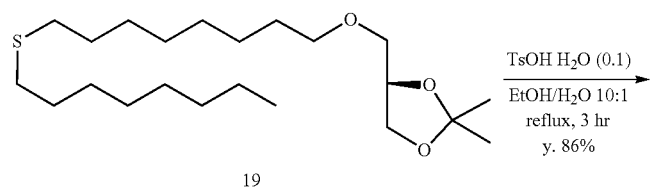
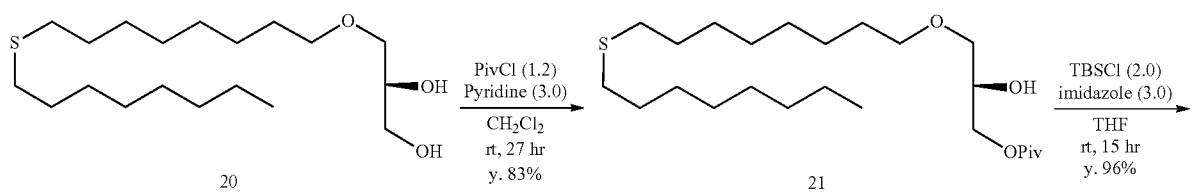
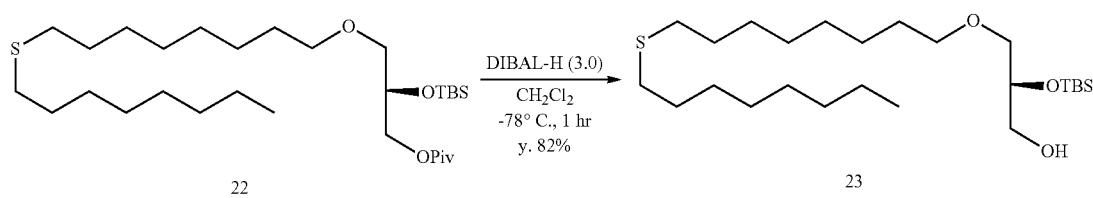
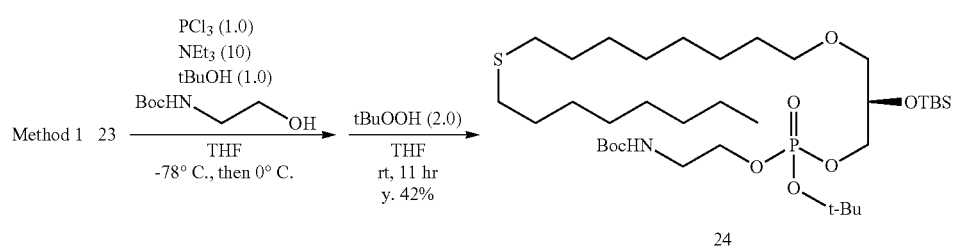
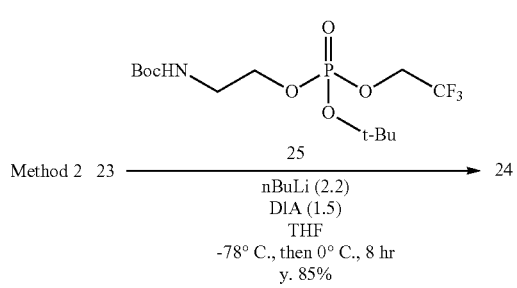
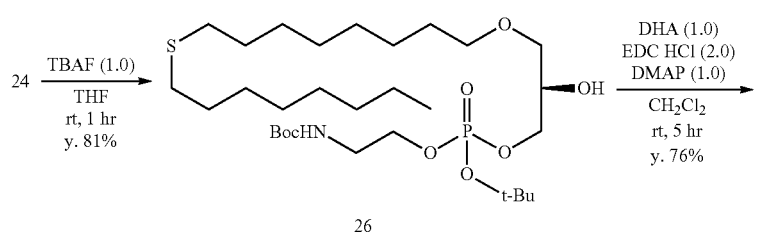

-continued

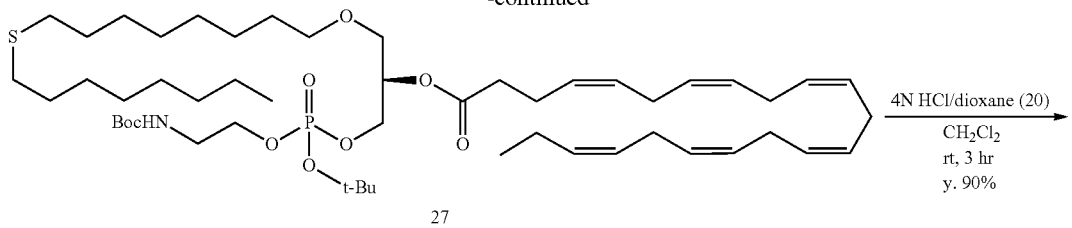

27

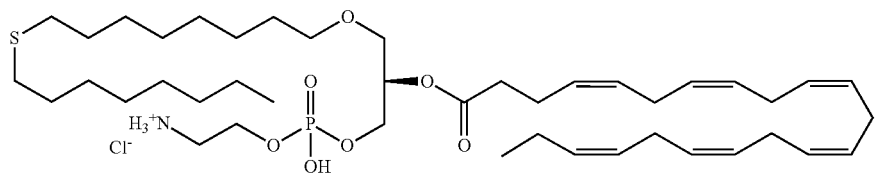

KIT-007-31-

Each step will be described specifically as follows.

[Step 1] Producing compound 17 presented by the following structural formula

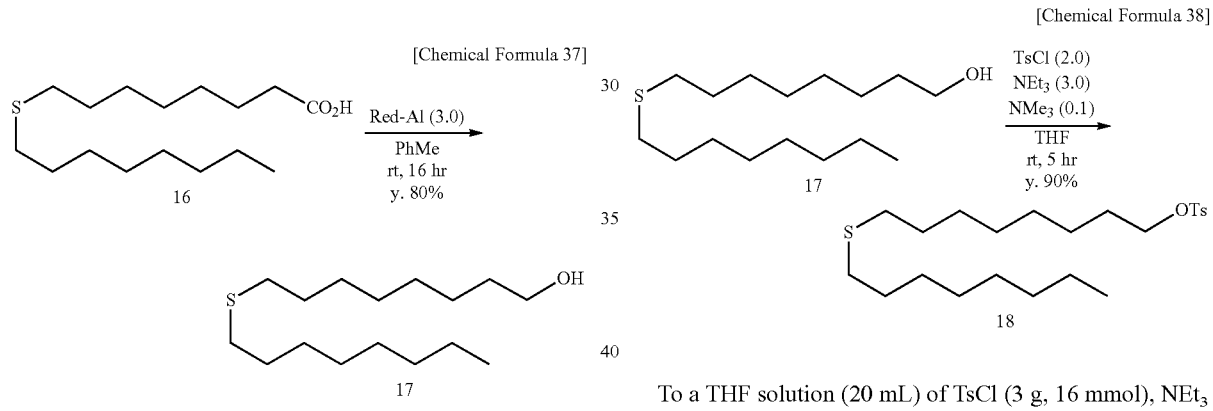

To a toluene (25 mL) of compound 16 (4 g, 14 mmol) was added a 12 mL of 70% toluene solution of Red-Al (sodium bis (2-methoxyethoxy) aluminum hydride) at 0° C. After being stirred for 16 hour at a room temperature, the reaction was quenched by addition of 1N HCl at 0° C. The precipitated solid was filtered off, the filtrate was concentrated, and the residue was purified by column chromatography on silica gel (Hex:AcOEt, 2:1) to yield compound 17 as a white solid (3 g, 80%).

$^1$H NMR (500 MHz; CDCl$_3$; Me$_4$Si) δ 3.64 (2H, t, J=6.6 Hz), 2.50 (4H, t, J=7.3 Hz), 1.61-1.53 (6H, m), 1.42-1.22 (19H, m), 0.88 (3H, t, J=7.0 Hz).

$^{13}$C NMR (126 MHz; CDCl$_3$; Me$_4$Si) δ 62.99, 32.74, 32.19, 32.15, 31.80, 29.71, 29.67, 29.26, 29.20, 29.18, 28.94, 28.84, 25.66, 22.63, 14.07

IR (ATR) 3345, 3264, 2919, 2848, 1459, 1378, 1278, 1225, 1189, 1130, 1050, 1021, 978, 748, 724 cm$^{-1}$.

MS (ESI) m/z 279 (M+Na$^+$).

HRMS (ESI) calcd for C16H34NaO1S1 (M+Na$^+$) 297.22281, found 297.22342.

[Step 2] Producing compound 18 presented by the following structural formula

To a THF solution (20 mL) of TsCl (3 g, 16 mmol), NEt$_3$ (3.5 mL, 24 mmol), and a 2M THF solution of NMe$_3$ (0.4 mL, 0.8 mmol) was added a THF solution (5 mL) of compound 17 (2.2 g, 8 mmol) at 0° C. After being stirred for 5 hour at a room temperature, the reaction was quenched by addition of water at 0° C. The mixture was extracted twice with ether. The combined extracts were washed with water and brine, dried over Na$_2$SO$_4$, and concentrated in vacuo. The residue was purified by column chromatography on silica gel (Hex:AcOEt, 9:1) to give compound 18 as a white solid (3.05 g, 90%).

$^1$H NMR (500 MHz; CDCl$_3$; Me$_4$Si) δ 7.79 (2H, d, J=8.5 Hz), 7.35 (2H, d, J=7.9 Hz), 4.01 (2H, t, J=6.6 Hz), 2.49 (2H, t, J=7.5 Hz), 2.48 (2H, t, J=7.3 Hz), 2.45 (3H, s), 1.63 (2H, quin, J=7.3 Hz), 1.60-1.51 (4H, m), 1.40-1.21 (18H, m), 0.88 (3H, t, J=7.0 Hz).

$^{13}$C NMR (126 MHz; CDCl$_3$; Me$_4$Si) δ 144.58, 133.24, 129.76, 127.84, 70.60, 32.20, 32.11, 31.80, 29.71, 29.60, 29.20, 29.18, 28.97, 28.94, 28.78, 28.73, 25.25, 22.62, 21.61, 14.07.

IR (ATR) 2918, 2851, 1597, 1468, 1355, 1307, 1173, 1097, 1049, 944, 816, 721, 665 cm$^{-1}$.

MS (ESI) m/z 451 (M+Na$^+$).

HRMS (ESI) calcd for C23H40NaO3S2 (M+Na$^+$) 451.23165, found 451.23225.

[Step 3] Producing compound 19 presented by the following structural formula

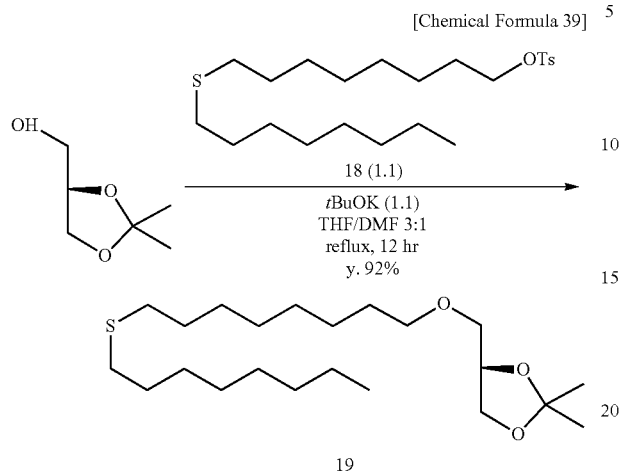

[Chemical Formula 39]

19

To a DMF solution (3.5 mL) of ′BuOK (862 mg, 7.7 mmol) was added a THF solution (3.5 mL) of (R)-(−)-2,2-dimethyl-1,3-dioxolane-4-methanol (925 mg, 7 mmol) at 0° C. After being stirred for 1 hour at 0° C., a THF solution (3.5 mL) of compound 18 (3 g, 7.7 mmol) was added to the mixture at 0° C. Then the mixture was refluxed for 12 hours. The reaction was quenched by addition of phosphate buffer (pH 7) at 0° C. The mixture was extracted twice with AcOEt. The combined extracts were washed with water and brine, dried over $Na_2SO_4$, and concentrated in vacuo. The residue was purified by column chromatography on silica gel (Hex: AcOEt, 10:1) to give compound 19 as a white solid (2.5 g, 92%).

$^1$H NMR (500 MHz; $CDCl_3$; $Me_4Si$) δ 4.26 (1H, quin, J=6.0 Hz), 4.06 (2H, dd, J=8.2, 6.4 Hz), 3.73 (1H, dd, J=8.2, 6.4 Hz), 3.53-3.40 (4H, m), 2.50 (4H, t, J=7.5 Hz), 1.61-1.53 (6H, m), 1.42 (3H, s), 1.36 (3H, s), 1.40-1.24 (18H, m), 0.88 (3H, t, J=7.0 Hz).

$^{13}$C NMR (126 MHz; $CDCl_3$; $Me_4Si$) δ 109.32, 74.74, 71.81, 66.92, 32.19, 32.15, 31.81, 29.72, 29.69, 29.52, 29.32, 29.21, 29.18, 28.95, 28.87, 26.76, 25.98, 25.41, 22.64, 14.08.

IR (ATR) 2923, 2853, 1457, 1378, 1255, 1212, 1117, 1054, 845, 723 $cm^{-1}$.

MS (ESI) m/z 411 ($M+Na^+$).

HRMS (ESI) calcd for $C_{22}H_{44}Na_1O_3S_1$ ($M+Na^+$) 411.29088, found 411.29101.

[Step 4] Producing compound 20 presented by the following structural formula

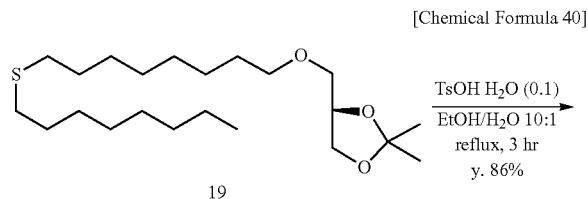

[Chemical Formula 40]

20

Compound 19 (2.35 mg, 6.0 mmol) was dissolved in EtOH (12 mL) and $H_2O$ (1.2 mL). To the solution was added $TsOH·H_2O$ (114 mg, 6.0 mmol) at 0° C. Then the mixture was refluxed for 3 hours. The reaction was quenched by addition of $NEt_3$ (0.4 mL, 3.0 mmol) at 0° C. The mixture was concentrated in vacuo and the residue was purified by column chromatography on silica gel (Hex:AcOEt, 1:3) to give compound 20 as a white solid (1.8 g, 86%).

$^1$H NMR (500 MHz; $CDCl_3$; $Me_4Si$) δ 3.89-3.83 (1H, m), 3.72 (1H, ddd, J=11.3, 7.2, 4.0 Hz), 3.65 (1H, dt, $J_d$=11.3 Hz, $J_t$=5.2 Hz), 3.53 (11H, dd, J=9.8, 4.0 Hz), 3.50 (1H, dd, J=9.8, 6.1 Hz), 3.48-3.44 (2H, m), 2.67 (1H, d, J=4.9 Hz), 2.50 (4H, t, J=7.5 Hz), 2.26 (1H, dd, J=7.1, 5.2 Hz), 1.61-1.53 (6H, m), 1.41-1.22 (18H, m), 0.88 (3H, t, J=7.0 Hz).

$^{13}$C NMR (126 MHz; $CDCl_3$; $Me_4Si$) δ 72.48, 71.77, 70.40, 64.26, 32.19, 32.15, 31.80, 29.71, 29.66, 29.52, 29.28, 29.20, 29.18, 29.15, 28.94, 28.84, 26.00, 22.63, 14.07.

IR (ATR) 3388, 3308, 3226, 2919, 2849, 1459, 1437, 1123, 1085, 1033, 871, 727 $cm^{-1}$.

MS (ESI) m/z 371 ($M+Na^+$).

HRMS (ESI) calcd for $C_{19}H_{40}Na_1O_3S_1$ ($M+Na^+$) 371.25958, found 371.25964.

[Step 5] Producing compound 21 presented by the following structural formula

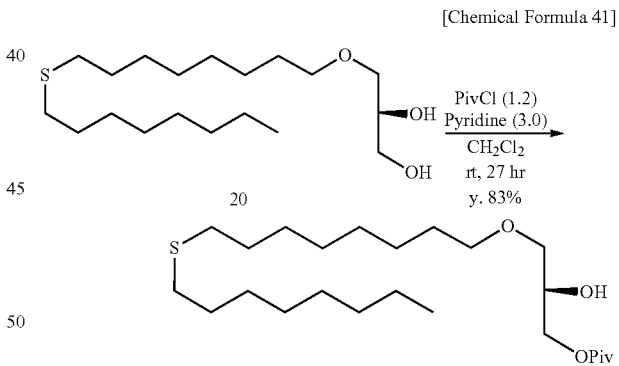

[Chemical Formula 41]

21

To a mixture of pyridine (0.35 mL, 4.2 mmol) and compound 20 (500 mg, 1.4 mmol) was added PivCl (0.2 mL, 1.68 mmol) at 0° C. After being stirred for 27 hours at 0° C., the reaction was quenched by addition of phosphate buffer (pH 7) at 0° C. The mixture was extracted twice with $CH_2Cl_2$. The combined extracts were washed with 2N HCl and saturated aqueous $NaHCO_3$, dried over $Na_2SO_4$, and concentrated in vacuo. The residue was purified by column chromatography on silica gel (Hex:AcOEt, 4:1) to give compound 21 as a colorless oil (500 mg, 83%).

$^1$H NMR (500 MHz; $CDCl_3$; $Me_4Si$) δ 4.16 (1H, dd, J=11.3, 4.9 Hz), 4.13 (1H, dd, J=11.7, 6.0 Hz), 4.02-3.96 (1H, m), 3.49 (1H, dd, J=9.6, 4.4 Hz), 3.49-3.43 (2H, m), 3.42 (1H, dd, J=9.6, 6.3 Hz), 2.50 (4H, t, J=7.5 Hz), 2.49 (1H, s), 1.57 (6H, quint, J=7.5 Hz), 1.41-1.23 (18H, m), 1.22 (9H, s), 0.88 (3H, t, J=7.0 Hz).

$^{13}$C NMR (126 MHz; CDCl$_3$; Me$_4$Si) δ (contains some overlapping peaks) 178.57, 71.66, 71.40, 68.92, 65.40, 38.81, 32.19, 32.15, 31.80, 29.71, 29.67, 29.53, 29.30, 29.20, 29.17, 28.94, 28.85, 27.16, 25.99, 22.62, 14.07.

IR (ATR) 3451, 2924, 2853, 1730, 1458, 1396, 1365, 1283, 1159, 1120, 1035 cm$^{-1}$.

MS (ESI) m/z 455 (M+Na$^+$).

HRMS (ESI) calcd for C$_{24}$H$_{48}$Na$_1$O$_4$S$_1$ (M+Na$^+$) 455.31710, found 455.31721.

[Step 6] Producing compound 22 presented by the following structural formula

[Chemical Formula 42]

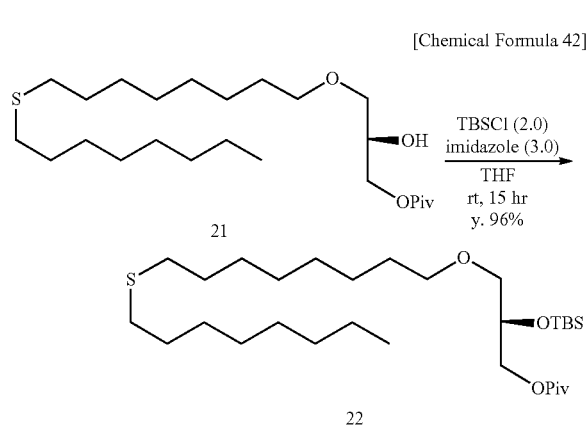

To a THF solution (15 mL) of TBSCl (1.4 g, 9.6 mmol) and imidazole (1 g, 14 mmol) was added a THF solution (5 mL) of compound 21 (2.1 g, 4.8 mmol) at 0° C. After being stirred for 15 hour at a room temperature, the reaction was quenched by addition of phosphate buffer (pH 7) at 0° C. The mixture was extracted twice with ether. The combined extracts were washed with water and brine, dried over Na$_2$SO$_4$, and concentrated in vacuo. The residue was purified by column chromatography on silica gel (Hex:AcOEt, 20:1) to give compound 22 as a colorless oil (2.35 g, 96%).

$^1$H NMR (500 MHz; CDCl$_3$; Me$_4$Si) δ 4.18-4.12 (1H, m), 4.01-3.95 (2H, m), 3.41 (2H, dt, J$_d$=1.6 Hz, J$_f$=6.6 Hz), 3.39 (1H, d, J=5.8 Hz), 2.50 (4H, t, J=7.5 Hz), 1.60-1.52 (6H, m), 1.40-1.23 (18H, m), 1.21 (9H, s), 0.88 (3H, t, J=6.9 Hz), 0.88 (9H, s), 0.09 (6H, s).

$^{13}$C NMR (126 MHz; CDCl$_3$; Me$_4$Si) δ (contains some overlapping peaks) 178.36, 72.45, 71.69, 69.69, 66.19, 38.77, 32.20, 32.18, 31.81, 29.74, 29.72, 29.63, 29.35, 29.22, 29.19, 28.96, 28.89, 27.24, 26.05, 25.73, 22.64, 18.05, 14.08, −4.64, −4.82.

IR (ATR) 2926, 2854, 1732, 1460, 1282, 1251, 1119, 1004, 831, 776 cm$^{-1}$.

MS (ESI) m/z 569 (M+Na$^+$).

HRMS (ESI) calcd for C$_{30}$H$_{62}$Na$_1$O$_4$S$_1$Si$_1$ (M+Na$^+$) 569.40358, found 569.40485.

[Step 7] Producing compound 23 presented by the following structural formula

[Chemical Formula 43]

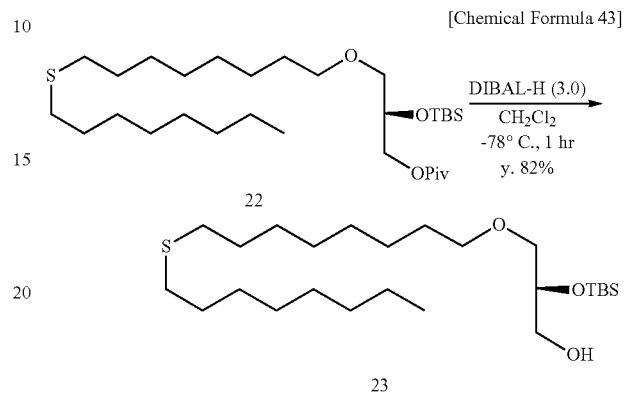

To a CH$_2$Cl$_2$ solution (30 mL) of compound 22 (2.2 g, 4.0 mmol) was added a 1M toluene solution of DIBAL-H (12 mL, 12 mmol) at −78° C. After being stirred for 1 hour at −78° C., the temperature was raised to 0° C. and then the reaction was quenched by sequential addition of 2 mL of water, 2 mL of 15% aqueous sodium hydroxide solution, and 6 mL of water at 0° C. The precipitated solid was filtered off and the filtrate was concentrated. The residue was purified by column chromatography on silica gel (Hex:AcOEt, 9:1) to give compound 23 as a colorless oil (1.51 g, 82%).

$^1$H NMR (500 MHz; CDCl$_3$; Me$_4$Si) δ 3.91-3.86 (1H, m), 3.64 (1H, dt, J$_d$=11.0 Hz, J$_f$=4.9 Hz), 3.58 (1H, ddd, J=11.1, 7.5, 4.6 Hz), 3.45-3.39 (4H, m), 2.50 (4H, t, J=7.5 Hz), 2.13 (1H, dd, J=7.3, 5.2 Hz), 1.61-1.52 (6H, m), 1.41-1.23 (18H, m), 0.90 (9H, s), 0.88 (3H, t, J=7.0 Hz), 0.099 (3H, s), 0.096 (3H, s).

$^{13}$C NMR (126 MHz; CDCl$_3$; Me$_4$Si) δ (contains some overlapping peaks) 72.77, 71.71, 71.16, 65.09, 32.20, 32.16, 31.80, 29.73, 29.70, 29.61, 29.31, 29.21, 29.18, 29.17, 28.95, 28.87, 26.03, 25.78, 22.63, 18.10, 14.07, −4.61, −4.88.

IR (ATR) 2925, 2853, 1462, 1251, 1115, 1048, 1004, 834, 776, 722, 669 cm$^{-1}$.

MS (ESI) m/z 485 (M+Na$^+$).

HRMS (ESI) calcd for C$_{25}$H$_{54}$Na$_1$O$_3$S$_1$Si$_1$ (M+Na$^+$) 485.34606, found 485.34768.

[Step 8] Producing compound 24 presented by the following structural formula. (Method 1)

[Chemical Formula 44]

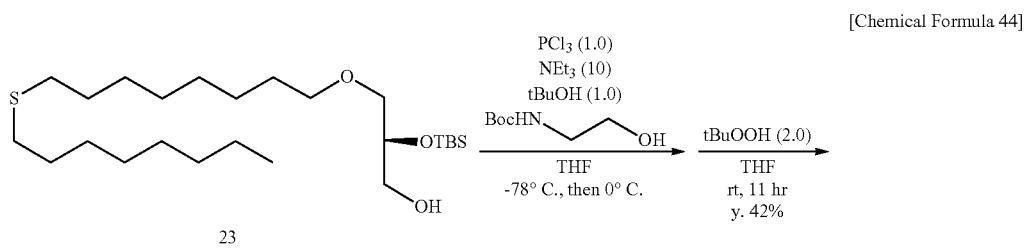

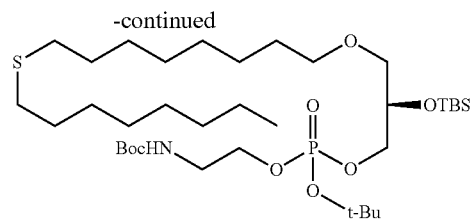

24

To a THF solution (26 mL) of Et$_3$N (3.7 mL, 26 mmol) was added PCl$_3$ (0.22 mL, 2.6 mmol) at −78° C. After being stirred for 30 minutes at −78° C., a THF solution (5 mL) of $^t$BuOH (193 mg, 2.6 mmol) was added to the mixture at −78° C. and the mixture was stirred for 1 hour at −78° C. Then compound 23 (1.2 g, 2.6 mmol) was added to the mixture. The resulting mixture was stirred at −78° C. until complete disappearance of compound 23 by a TLC analysis (silica gel, Hex:AcOEt, 9:1). To the mixture was added a THF solution (5 mL) of N-Boc-ethanolamine (503 mg, 3.12 mmol) at −78° C. and then the temperature was raised to 0° C. After being stirred for 1 hour at 0° C., the precipitated solid was filtered off and the filtrate was concentrated in vacuo. The residue was dissolved in THF (26 mL), and a 70% aqueous solution of $^t$BuOOH (670 mg, 5.2 mmol) was added to the solution at 0° C. The resulting mixture was stirred at a room temperature for 11 hour, and then the reaction was quenched by addition of saturated aqueous NaS$_2$O$_3$ solution at a room temperature. The mixture was extracted twice with AcOEt, and the combined extracts were washed with brine, dried over Na$_2$SO$_4$, and concentrated in vacuo. The residue was purified by column chromatography on silica gel (Hex:AcOEt, 2:1) to give compound 24 as a diastereomer mixture (820 mg, 42%).

Producing compound 24 presented by the following structural formula (Method 2)

mg, 0.43 mmol) was added to the mixture at −78° C. The temperature was raised to 0° C. and the mixture was stirred for 8 hour at 0° C. The reaction was quenched by addition of phosphate buffer (pH 7), and the mixture was extracted twice with AcOEt. The combined extracts were washed with water and brine, dried over Na$_2$SO$_4$, and concentrated in vacuo. The residue was purified by column chromatography on silica gel (Hex:AcOEt, 3:2) to give compound 24 as a diastereomer mixture (225 mg, 85%).

$^1$H NMR (500 MHz; CDCl$_3$; Me$_4$Si) δ 5.18 (1H, brs), 4.08-4.00 (3H, m), 3.99-3.94 (1H, m), 3.93-3.87 (1H, m), 3.43-3.36 (6H, m), 2.50 (4H, t, J=7.5 Hz), 1.60-1.52 (6H, m), 1.505 (9H×0.5, s, one diastereomer), 1.502 (9H×0.5, s, the other diastereomer), 1.44 (9H, s), 1.41-1.23 (18H, m), 1.21 (9H, s), 0.89 (9H, s), 0.88 (3H, t, J=7.0 Hz), 0.88 (9H, s), 0.10 (3H×0.5, s, one diastereomer), 0.093 (3H×0.5, s, the other diastereomer), 0.088 (3H, s).

$^{13}$C NMR (126 MHz; CDCl$_3$; Me$_4$Si) δ (contains some overlapping peaks) 155.79, 83.39 (d, J$_{C-P}$=7.3 Hz, one diastereomer), 83.33 (d, J$_{C-P}$=8.3 Hz, the other diastereomer), 79.39, 71.95 (d, J$_{C-P}$=4.2 Hz), 71.72, 70.53 (d, J$_{C-P}$=8.3 Hz), 68.63 (d, J$_{C-P}$ 6.2 Hz), 66.57 (brs), 40.97 (d, J$_{C-P}$=6.2 Hz), 32.20, 32.18, 31.81, 29.82, 29.80, 29.73, 29.71, 29.64, 29.37, 29.21, 28.96, 28.90, 28.38, 26.05, 25.77, 22.64, 18.13, 14.08, −4.74. $^{31}$P NMR (202 MHz,

[Chemical Formula 45]

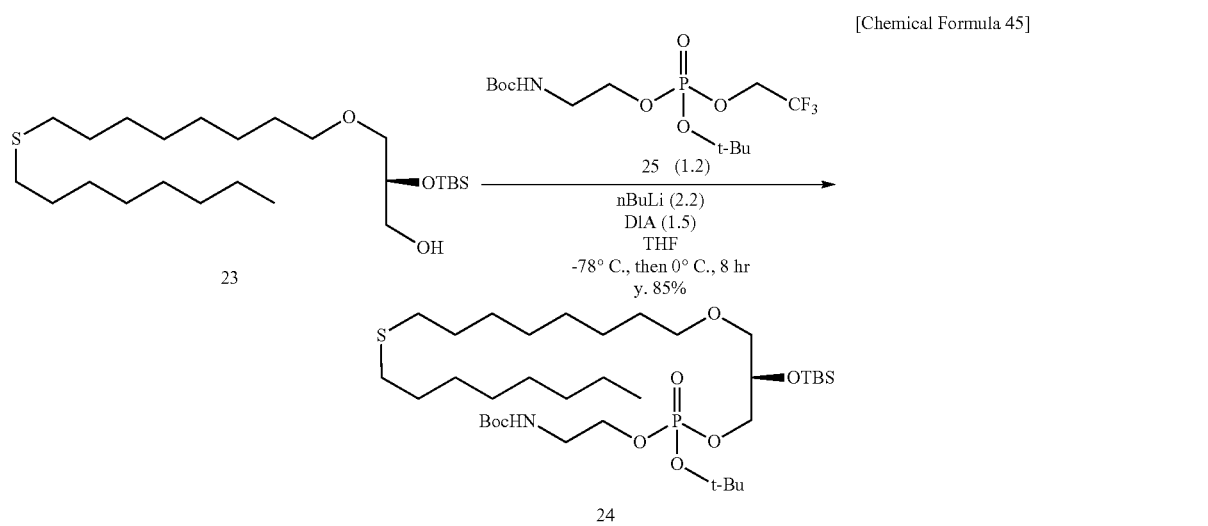

To a toluene solution (1.0 mL) of compound 23 (165 mg, 0.36 mmol) and diisopropylamine (0.08 mL, 0.54 mmol) was added a 1.55M hexane solution of butyl lithium (0.5 mL, 0.76 mmol) at −78° C. After being stirred for 1 hour at −78° C., a toluene solution (1.0 mL) of compound 25 (162

CDCl$_3$, External standard: 85% H$_3$PO$_4$) δ-4.67 (one diastereomer), −4.76 (the other diastereomer).

IR (ATR) 2926, 2854, 1732, 1460, 1282, 1251, 1119, 1004, 831, 776 cm$^{-1}$.

MS (ESI) m/z 569 (M+Na$^+$).

HRMS (ESI) calcd for $C_{30}H_{62}Na_1O_4S_1Si_1$ (M+Na$^+$) 569.40358, found 569.40485.

[Step 9] Producing compound 26 presented by the following structural formula

[Chemical Formula 46]

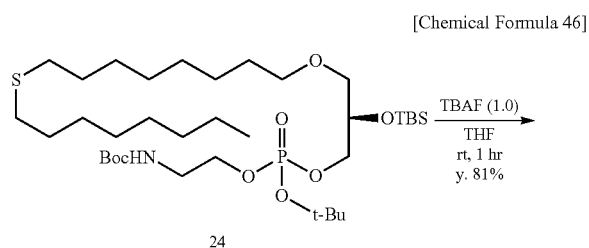

To a THF solution (5 mL) of compound 24 (350 mg, 0.47 mmol) was added a 1M THF solution of TBAF (0.5 mL, 0.5 mmol) at 0° C. After being stirred for 5 hours at a room temperature, the reaction was quenched by addition of phosphate buffer (pH 7) at a room temperature. The mixture was extracted twice with AcOEt. The combined extracts were washed with water and brine, dried over $Na_2SO_4$, and concentrated in vacuo. The residue was purified by column chromatography on silica gel (Hex:AcOEt, 1:4) to give compound 26 as an approximately 1:1 diastereomer mixture (240 mg, 81%).

$^1$H NMR (500 MHz; CDCl$_3$; Me$_4$Si) δ5.23 (1H, brs), 4.15-3.96 (m, 5H), 3.48 (2H, d, J=5.5 Hz), 3.45 (2H, t, J=6.7 Hz), 3.43-3.35 (2H, m), 3.27 (1H, br), 2.50 (4H, t, J=7.5 Hz), 1.61-1.53 (6H, m), 1.51 (9H, s), 1.44 (9H, s), 1.41-1.24 (18H, m), 0.88 (3H, t, J=7.0 Hz).

$^{13}$C NMR (126 MHz; CDCl$_3$; Me$_4$Si) δ (contains some overlapping peaks) 155.76, 83.89 (d, $J_{C-P}$=5.2 Hz, one diastereomer), δ3.84 (d, $J_{C-P}$ 6.2 Hz, the other diastereomer), 79.42, 71.66, 70.81, 69.37-69.29 (several peaks), 68.77 (d, $J_{C-P}$=6.2 Hz), 66.68 (brs), 40.83 (d, $J_{C-P}$=6.2 Hz), 32.13, 32.10, 31.75, 29.75, 29.71, 29.66, 29.63, 29.50, 29.28, 29.15, 29.13, 28.89, 28.82, 28.32, 25.95, 22.57, 14.03.

$^{31}$P NMR (202 MHz, CDCl$_3$, External standard: 85% $H_3PO_4$) δ −3.89.

IR (ATR) 3348, 2924, 2854, 1713, 1522, 1458, 1366, 1250, 1171, 1117, 998 cm$^{-1}$.

MS (ESI) m/z 650 (M+Na$^+$).

HRMS (ESI) calcd for $C_{30}H_{62}N_1Na_1O_8P_1S_1$ (M+Na$^+$) 650.38314, found 650.38294.

[Step 10] Producing compound 27 presented by the following structural formula

[Chemical Formula 47]

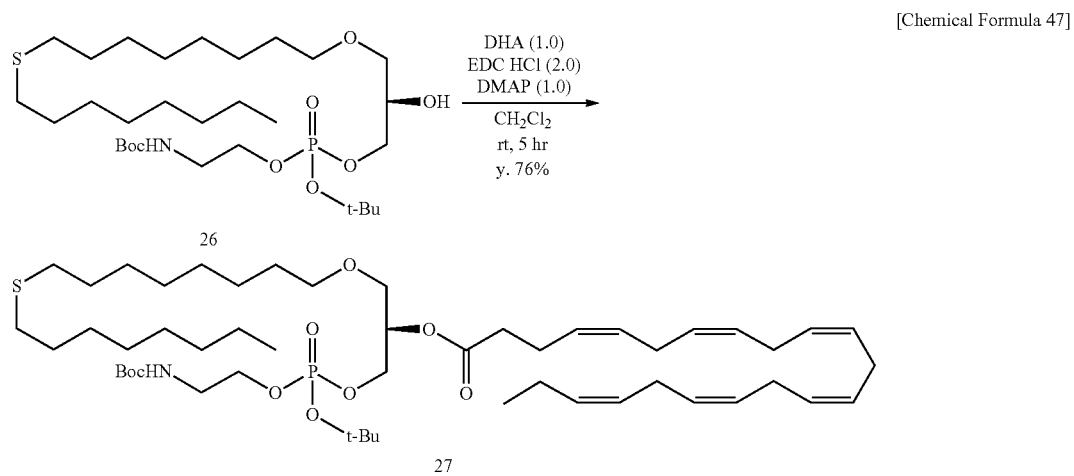

To a CH$_2$Cl$_2$ solution (3 mL) of compound 26 (240 mg, 0.38 mmol), DHA (125 mg, 0.38 mmol), and DMAP (46 mg, 0.38 mmol) was added EDC·HCl (145 mg, 0.76 mmol) at 0° C. After being stirred for 5 hours at a room temperature, the reaction mixture was concentrated in vacuo and the residue was purified by column chromatography on silica gel (Hex:AcOEt, 1:2) to give compound 27 as an approximately 1:1 diastereomer mixture (270 mg, 76%).

$^1$H NMR (500 MHz; CDCl$_3$; Me$_4$Si) δ 5.43-5.28 (12H, m), 5.16 (br, 1H), 5.16 (1H, quin. J=5.0 Hz), 4.21-4.16 (1H, m), 4.15-4.09 (1H, m) 4.07-4.02 (2H, m), 3.55 (2H, d, J=5.2 Hz), 3.47-3.36 (4H, m), 2.87-2.78 (10H, m), 2.49 (4H, t, J=7.5 Hz), 2.42-2.39 (4H, m), 2.07 (2H, quin, J=7.4 Hz), 1.60-1.52 (m, 6H), 1.504 (9H×0.5, s, one diastereomer), 1.496 (9H×0.5, s, the other diastereomer), 1.44 (9H, s), 1.40-1.24 (18H, m), 0.97 (3H, t, J=7.5 Hz), 0.88 (3H, t, J=6.9 Hz).

$^{13}$C NMR (126 MHz; CDCl$_3$; Me$_4$Si) S (contains some overlapping peaks) 172.29, 155.73, 131.96, 129.31, 128.51, 128.24, 128.22, 128.19, 128.03, 128.01, 127.97, 127.80, 127.69, 126.95, 83.75 (d, $J_{C-P}$=7.3 Hz, one diastereomer), 83.67 (d, $J_{C-P}$=7.3 Hz, the other diastereomer), 79.39, 71.71, 70.82 (d, $J_{C-P}$=8.3 Hz), 68.30, 66.66, 65.40 (d, $J_{C-P}$=5.2 Hz), 40.89 (d, $J_{C-P}$=5.2), 34.06, 32.15, 32.12, 31.77, 29.75, 29.71, 29.69, 29.67, 29.49, 29.31, 29.18, 29.15, 28.92, 28.86, 28.34, 25.93, 25.59, 25.54, 25.49, 22.60, 20.51, 14.23, 14.05.

$^{31}$P NMR (202 MHz, CDCl$_3$, External standard: 85% H$_3$PO$_4$) δ −4.73 (one diastereomer), −4.83 (the other diastereomer).

IR (ATR) 3011, 2925, 2853, 1738, 1714, 1517, 1457, 1366, 1267, 1170, 1000 cm$^{-1}$

MS (ESI) m/z 960 (M+Na$^+$).

HRMS (ESI) calcd for C$_{52}$H$_{92}$N$_1$Na$_1$O$_9$P$_1$S$_1$ (M+Na$^+$) 960.61281, found 960.61212.

[Step 11] Producing compound KIT-007 according to the present invention presented by the following structural formula

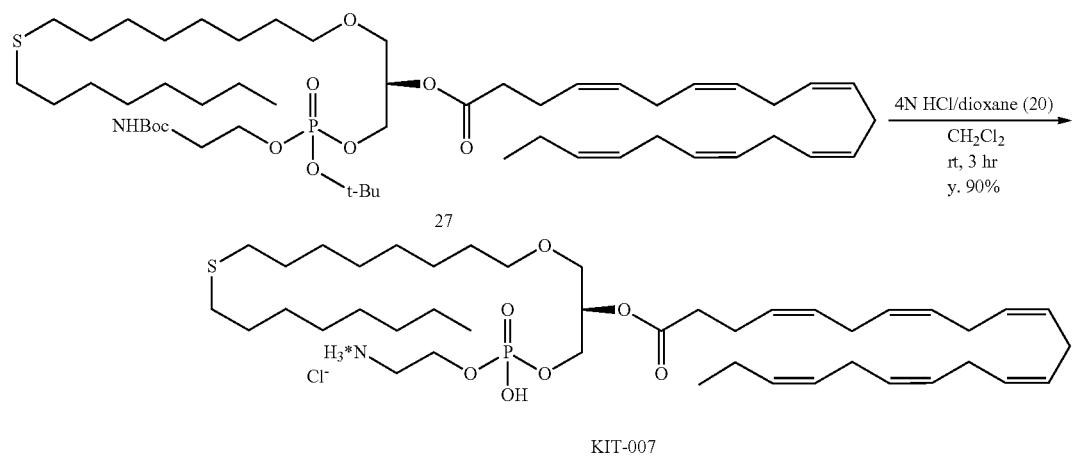

KIT-007

To a CH$_2$Cl$_2$ solution (1.5 mL) of compound 27 (70 mg, 0.075 mmol) added a 4M 1,4-dioxane solution of hydrogen chloride (0.38 mL, 1.52 mmol) at 0° C. After being stirred for 3 hours at a room temperature, the reaction mixture was concentrated in vacuo to give compound KIT-007 as a yellow oil (55 mg, 90%).

$^1$H NMR (500 MHz; CDCl$_3$; Me$_4$Si) δ 10.46 (1H, br), 8.18 (3H, brs), 5.43-5.28 (12H, m), 5.14 (1H, brs), 4.31-4.21 (2H, m), 4.13-4.02 (2H, m), 3.58-3.50 (2H, m), 3.47-3.25 (4H, m), 2.89-2.78 (m, 10H), 2.49 (4H, t, J=7.5 Hz), 2.45-2.33 (4H, m), 2.08 (2H, quin, J=7.4 Hz), 1.60-1.49 (6H, m), 1.41-1.21 (18H, m), 0.97 (3H, t, J=7.5 Hz), 0.88 (3H, t, J=6.9 Hz).

$^{13}$C NMR (126 MHz; CDCl$_3$; Me$_4$Si) δ (contains some overlapping peaks) 172.44, 131.95, 129.25, 128.51, 128.25, 128.23, 128.21, 128.04, 128.01, 127.80, 126.96, 71.73, 71.04 (d, J$_{C-P}$=8.3 Hz), 68.60, 65.49, 62.94 (d, J$_{C-P}$ 8.3 Hz), 40.28 (d, J$_{C-P}$=6.2 Hz), 34.08, 32.17, 32.15, 31.78, 29.69, 29.54, 29.38, 29.23, 29.19, 29.16, 28.93, 25.95, 25.59, 25.49, 22.61, 20.51, 14.24, 14.06.

$^{31}$P NMR (202 MHz, CDCl$_3$, External standard: 85% H$_3$PO$_4$) δ 0.95.

IR (ATR) 3012, 2924, 2853, 1735, 1683, 1526, 1457, 1374, 1204, 1132, 1076, 1026 cm$^{-1}$

MS (ESI) m/z 804 (M-HCl+Na$^+$).

HRMS (ESI) calcd for C$_{43}$H$_{76}$N$_1$Na$_1$O$_7$P$_1$S$_1$ (M-HCl+Na$^+$) 804.49778, found 804.49691.

As described in the above, synthesis examples of new compounds according to the present invention were illustrated. However, the present invention is not limited to them. For example, with respect to a compound according to the present invention having both a hetero atom in a carbon chain of an sn-1 position and vinyl ether bond, it is considered as a possible synthesis to apply a step transforming from compound 4 to compound 5 disclosed in P. Wang et al, "Improved Plasmalogen Synthesis Using Organobarium Intermediates," J. Org. Chem, 72: 5005-5007, 5006 (2007) (Non-patent Document 10).

Example 4

By using a neuronal cell line, a study was performed with respect to enhanced phosphorylation activities of ERK (ERK1/2) with compounds according to the present invention.

[TRIAL 1]

Neuronal cell lines (mouse neuroblastoma derived NEURO2A cell and human neuroblastoma derived SH-SY5Y cell) were cultivated in DMEM medium containing 10% FBS (fetal bovine serum) for 24 hours. Subsequently, they were cultivated in DMEM medium containing 2% FBS for overnight (18 hours), which were then processed with 5 µg/ml of s-Pls (scallop-derived Pls), Compound REO-002 according to the present invention, and Compound REO-003 according to the present invention for 30 minutes respectively, and cells were subjected to Western Blotting assay. At this stage, the same amount of protein (50 µg of protein extracts) was subjected to an analysis to compare phosphorylation of ERK (ERK ½) (p-ERK).

The results were shown in FIG. 1. As FIG. 1 shows, both REO-002 and REO-003 exhibit enhanced phosphorylation activities of ERK (ERK½) equivalent to s-Pls in neuronal cell lines.

[TRIAL 2]

Neuronal cell lines (human neuroblastoma derived SH-SY5Y cell) were cultivated in DMEM medium containing 10% FBS (fetal bovine serum) for 24 hours. Subsequently, they were cultivated in DMEM medium containing 2% FBS for overnight (18 hours), which were then processed with 1 µg/ml, 5 µg/ml of Compounds REO-004-007 according to the present invention for 30 minutes respectively, and cells were subjected to Western Blotting assay. At this stage, the same amount of protein (50 µg of protein extracts) was subjected to an analysis to compare phosphorylation of ERK (ERK ½) (p-ERK).

Figure 2:
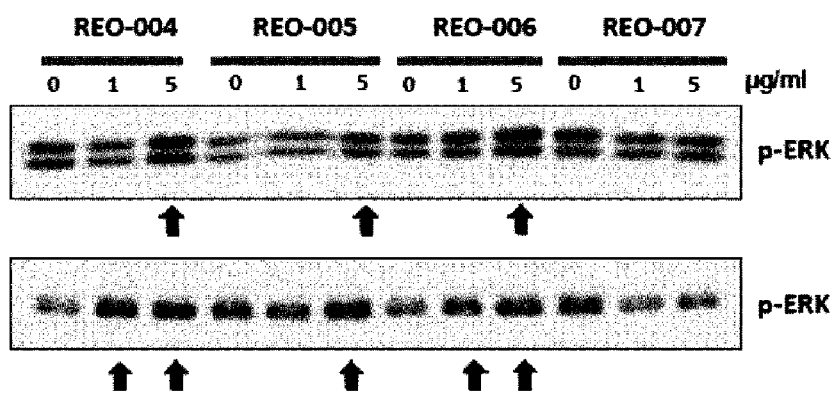
FIG. 2 shows enhanced phosphorylation activities of ERK (ERK1/2) in a neuronal cell line (human neuroblastoma derived SH-SY5Y cell) processed by Compounds (REO-004-007) according to the present invention.

The results were shown in FIG. 2. As a consequence of performing it twice, as the lower chart of FIG. 2 shows, 1 µg/ml of Compounds according to the present invention REO-004, REO-006 exhibit enhanced phosphorylation activities of ERK (ERK½) in SH-SY5Y cells (an arrow indicates a minimum effective dose). Since Compound according to the present invention REO-007 exhibits lower activities, it suggests that a length of sn-1 is a critical factor.

[TRIAL 3]

Neuronal cell lines (mouse neuroblastoma derived NEURO2A cell) were cultivated in DMEM medium containing 10% FBS (fetal bovine serum) for 24 hours. Subsequently, they were cultivated in DMEM medium containing 2% FBS for overnight (18 hours), which were then processed with 0.01 μg/ml-5 μg/ml of s-Pls (scallop-derived Pls), Compound KIT-007 according to the present invention for 20 minutes respectively, and cells were subjected to Western Blotting assay. At this stage, the same amount of protein (50 μg of protein extracts) was subjected to an analysis to compare phosphorylation of ERK (ERK %) (p-ERK).

Figure 3:
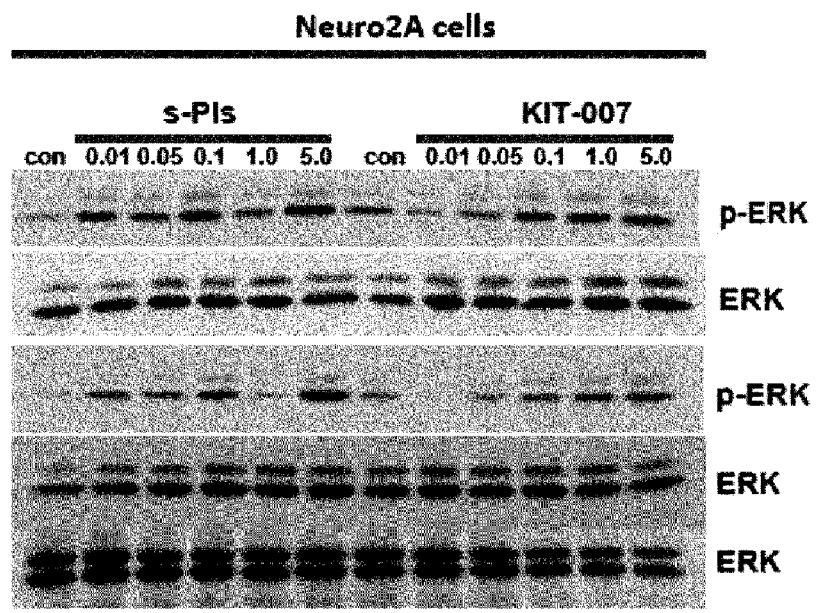
FIG. 3 shows enhanced phosphorylation activities of ERK (ERK1/2) in a neuronal cell line (mouse neuroblastoma derived Neuro 2A cell) processed by a compound (KIT-007) according to the present invention.

The results were shown in FIG. 3. As a consequence of performing it twice, both exhibit enhanced phosphorylation activities of ERK (ERK½) in Neuro2A cells.

Example 5

A study was performed with respect to an impact of Compound KIT-007 according to the present invention on a learning function and cognitive function of a young mouse.

Male C57BL/6J mice (3 months old) were used for an experiment. Mice were divided into two groups (n=3 (total 6 mice)), wherein an administered group was administered Compound KIT-007 according to the present invention dissolved in a tap water (1 mg/kg), while a control group was provided a tap water (2 months). After 2 months passed, a water maze test was performed three times per day.

Figure 4:
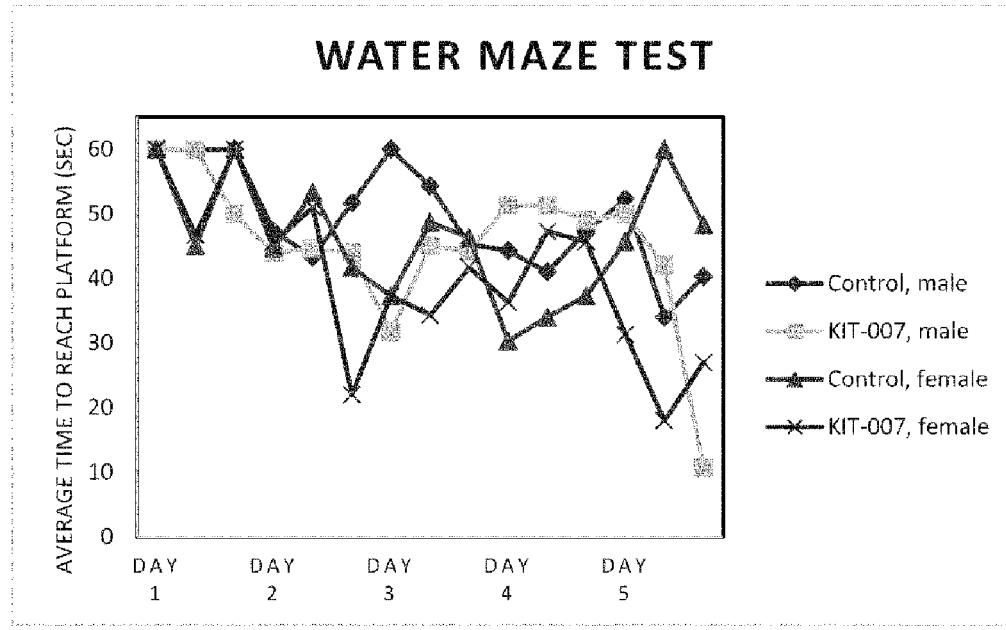
FIG. 4 shows a result of a water maze test to a young mouse administered a compound KIT-007 according to the present invention.

FIG. 4 shows the result. As FIG. 4 shows, using Compound KIT-007 according to the present invention enhanced both learning function and cognitive function of young mice.

Example 6

A study was performed with respect to an inhibiting effect of Compound KIT-007 according to the present invention against LPS-induced nerve inflammation in a mouse.

Male C58BL/6J mice (7 weeks old) were used for an experiment. Their weights ranged from 24.0 g to 26.7 g. They were randomized into five groups, and a reagent was injected into the abdominal cavity at 11:00-12:00 a.m. every day for 7 days.

Figure 5:
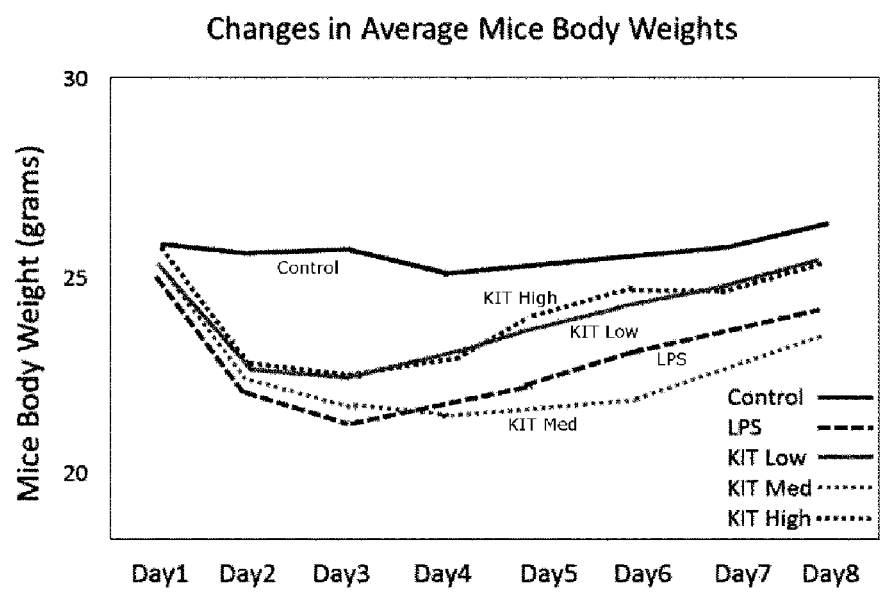
FIG. 5 shows a weight change by administration of a compound KIT-007 according to the present invention.

As a reagent, following 5 types were used: (1) normal saline as a control; (2) LPS dissolved in normal saline (LPS: 250 μg/kg); (3)-(5) Compound KIT-007 was added to the LPS solution at a predetermined concentration (low concentration (1 mg/kg); medium concentration (10 mf/kg); and high concentration (20 mg/kg). Their weights are recorded for 8 days (FIG. 5). On the $8^{th}$ day, mice were sacrificed.

By using a real-time PCR, inflammatory cytokine IL-1β and TNF-α were measured in prefrontal cortex (PFC) and hippocampal tissues (n=2).

Figure 6:
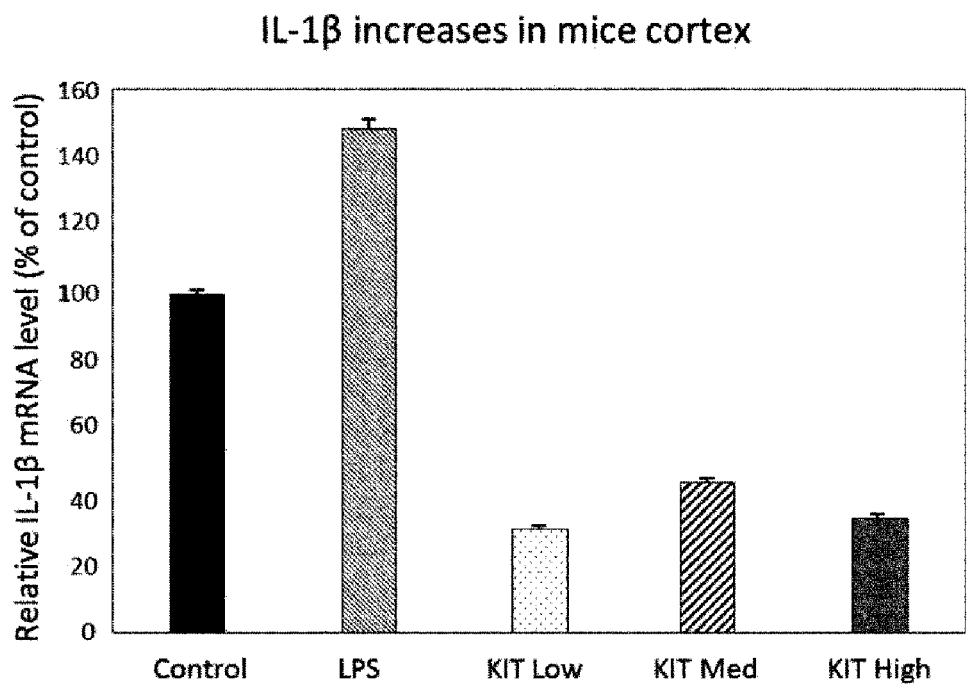
FIG. 6 shows a measurement result of inflammatory cytokine IL-10 in a prefrontal cortex (PFC) of a mouse administered a compound KIT-007 according to the present invention and LPS (real-time PCR).
Figure 7:
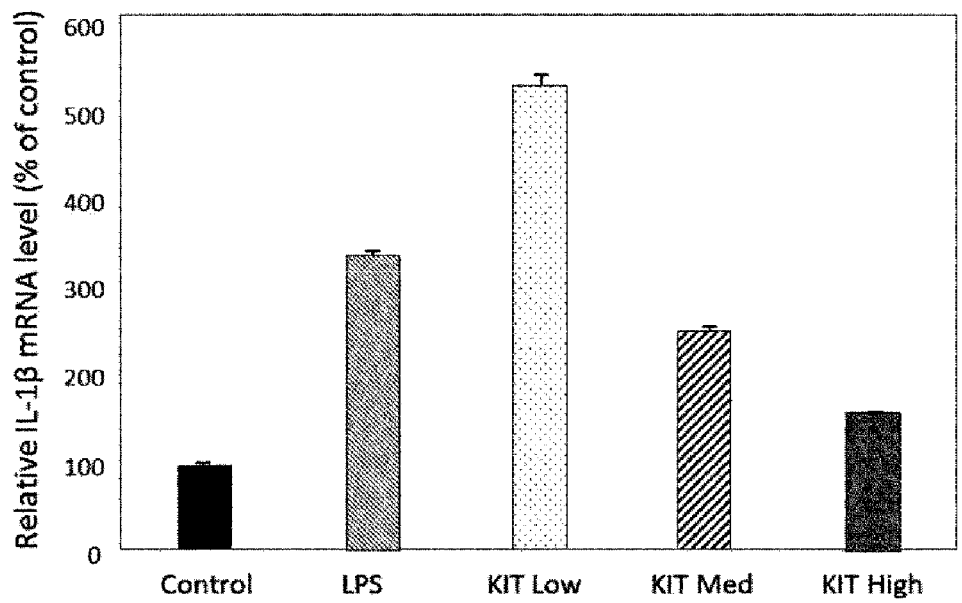
FIG. 7 shows a measurement result of inflammatory cytokine IL-1β in a hippocampus of a mouse administered a compound KIT-007 according to the present invention and LPS (real-time PCR).
Figure 8:
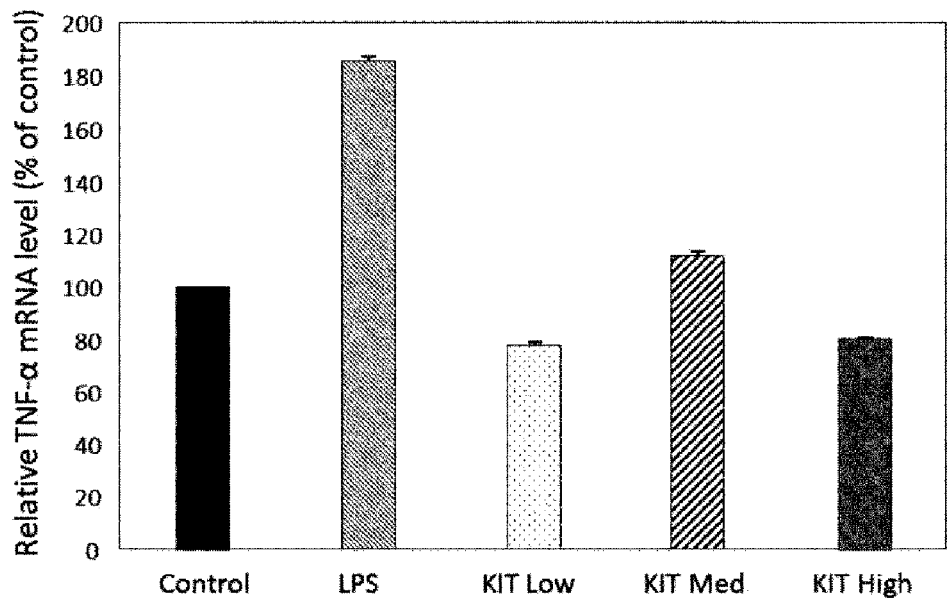
FIG. 8 shows a measurement result of inflammatory cytokine TNF-α in a prefrontal cortex (PFC) of a mouse administered a compound KIT-007 according to the present invention and LPS (real-time PCR).

The results are shown in FIGS. 6-8. As FIGS. 6-8 show, Compound KIT-007 according to the present invention exhibits an ameliorating effect against LPS-induced nerve inflammation.

Example 7

A study was performed with respect to an inhibiting effect of Compound REO-002 according to the present invention against LPS-induced nerve inflammation in a mouse.

Male C58BL/6J mice (6 months old) were used for an experiment. They were randomized into 4 groups, and a reagent was injected into the abdominal cavity at 9:00-10:00 a.m. every day for 7 days.

As a reagent, following 4 types were used: (1) normal saline as a control; (2) LPS dissolved in normal saline (LPS: 250 μg/kg); (3) the LPS solution added by Compound REO-002 in low concentrations (1 mg/kg); and (4) the LPS solution added by Compound REO-002 in high concentrations (5 mg/kg). On the 8th day since the experiment started, 3 mice were selected from each group randomly, sacrificed, to which transcardial perfusion was performed, their brains were extracted to provide immunohistochemical staining. In the meantime, on Day 1 and Day 4, water intake per day was measured for a mice of each group. In addition on Day 3, body weight was measured for a mice of each group.

Immunohistochemical staining was performed in a following manner:
a. An entire brain is fixed with 4% paraformaldehyde to perform OCT compound fixation after processing by saccharose anhydration;
b. Brain cortex and hippocampus parts are cut out by 20 m thickness and restored in PBS added by sodium azide;
c. After activating antigen by acidum hydrochloricum and neutralizing by Tris-HCL buffer, Iba-1 (microglial cell) and GFAP (astrocyte) are provided staining, nuclear staining.
d. Cell number and cell shape are confirmed by a fluorescence microscope.

Figure 9:
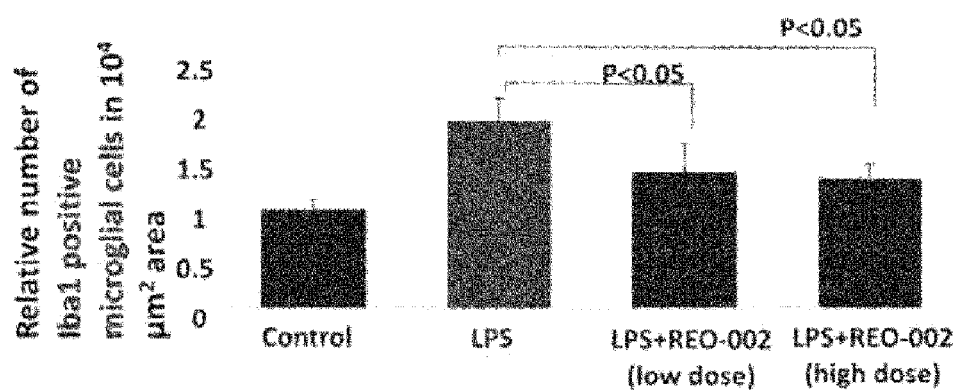
FIG. 9 shows a measurement result of Iba-1 positive microglia cells in a hippocampus of a mouse administered a compound REO-002 according to the present invention and LPS.
Figure 10:
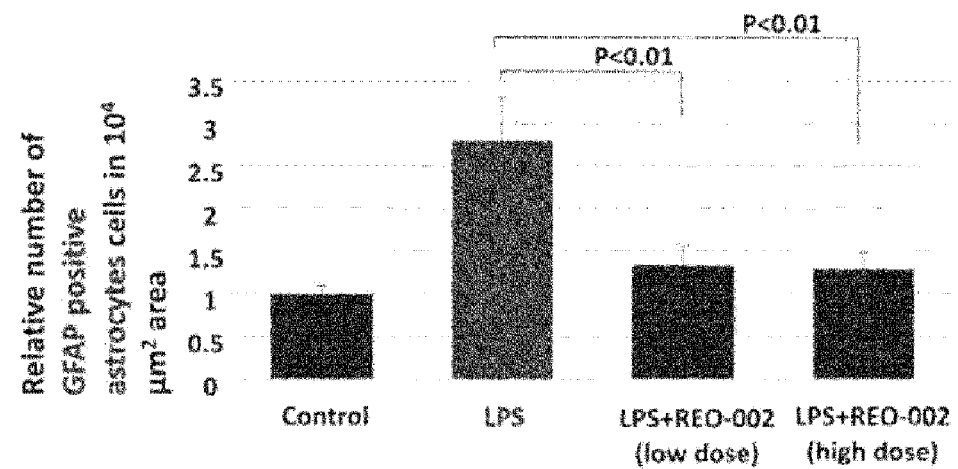
FIG. 10 shows a measurement result of GFAP positive astrocyte cells in a hippocampus of a mouse administered a compound REO-002 according to the present invention and LPS.

FIGS. 9 and 10 show an inhibiting effect of Compound REO-002 according to the present invention on activation of LPS-induced glia cells in a hippocampus tissue. As FIGS. 9 and 10 illustrate, Iba-1 positive microglia cells, GFAP positive astrocyte cells increased in number in a hippocampus tissue of LPS-administered group. However, such increase was inhibited for both in a group combined with Compound REO-2 according to the present invention (n=3, p<0.05 and p<0.01).

Figure 11:
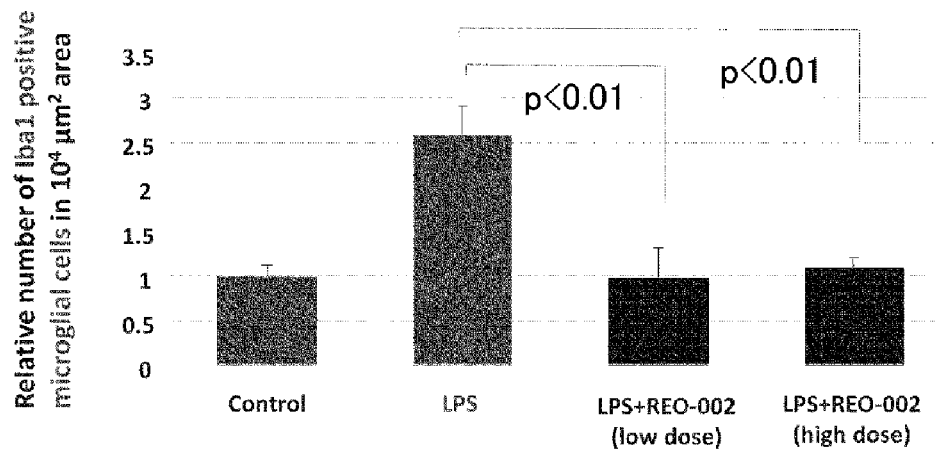
FIG. 11 shows a measurement result of Iba-1 positive microglia cells in a brain cortex of a mouse administered a compound REO-002 according to the present invention and LPS.

In addition, FIG. 11 shows an inhibiting effect of Compound REO-002 according to the present invention on activation of LPS-induced microglia cells in a brain cortex tissue. As FIG. 11 illustrates, Iba-1 positive microglia cells increased in number in a brain cortex tissue of LPS-administered group. However, such increase was inhibited in a group combined with Compound REO-2 according to the present invention to the equivalent extent of a controlled group (n=3, p<0.01).

Figure 12:
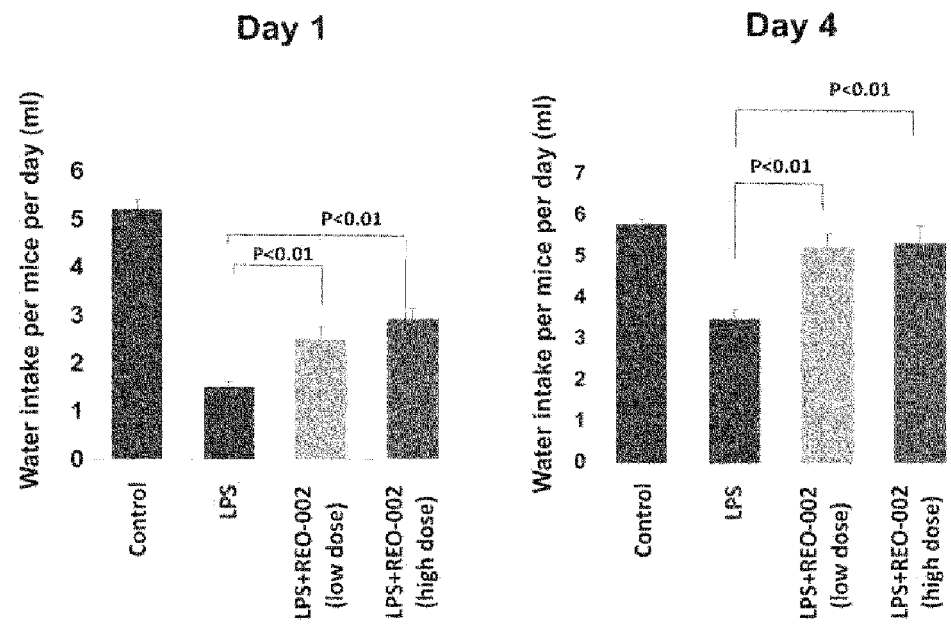
FIG. 12 shows a measurement result of water intake per day (Day 1 and Day 4) of a mouse administered a compound REO-002 according to the present invention and LPS.

FIG. 12 shows a result measuring water intake per day of a mouse of each group on Day 1 and Day 4. For an LPS-administered group, the water intake volume was decreased most a day after the administration, continued decreasing after 4 days. On the other hand, for a group combined with Compound REO-2 according to the present invention, such decrease was recovered dependent on dosage amount (n=5, p<0.01).

Figure 13:
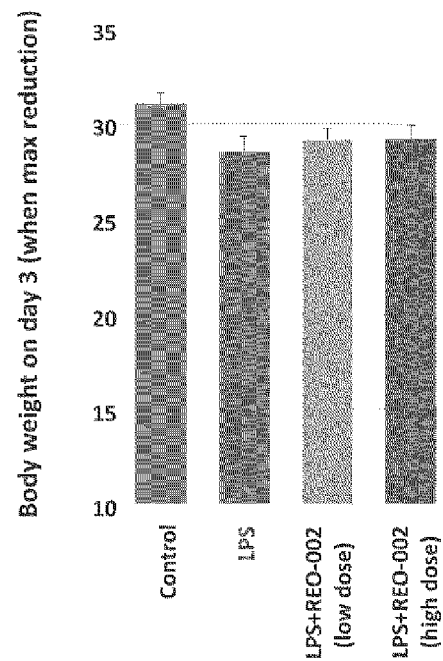
FIG. 13 shows a measurement result of body weight (on Day 3) of a mouse administered a compound REO-002 according to the present invention and LPS.

FIG. 13 shows a result measuring body weight of a mouse of each group on Day 3. For an LPS-administered group, the body weight was decreased most on Day 3 after the administration. On the other hand, for a group combined with Compound REO-2 according to the present invention, there was a tendency to show a recovery of such decrease dependent on dosage amount (n=5).

INDUSTRIAL APPLICABILITY

Since new compounds according to the present invention exhibit an effect equivalent to or beyond plasmalogens do, and since it is capable of being used for preventing or improving dementia, it is industrially applicable.

The invention claimed is:

1. A compound presented by Chemical Formula 1, a racemic form, or a salt thereof:

[Chemical Formula 1]

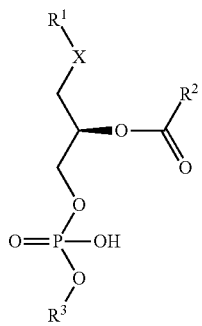
(I)

wherein,
X represents an oxygen atom, a nitrogen atom, a sulfur atom, or a carbon atom,
$R^1$ represents $R^{1a}$—Y—$R^{1b}$, wherein $R^{1a}$ and $R^{1b}$ each independently represent a saturated or an unsaturated aliphatic hydrocarbon group, an aromatic group, a heterocyclic group, or a combination thereof, Y represents an oxygen atom, a nitrogen atom, or a sulfur atom,
$R^2$ represents a saturated or unsaturated aliphatic hydrocarbon group, and
$R^3$ represents choline, ethanolamine, inositol, or serine.

2. The compound, racemic form, or salt thereof according to claim 1, wherein X is an oxygen atom.

3. The compound, racemic form, or salt thereof according to claim 2, wherein Y is an oxygen atom, or a nitrogen atom.

4. The compound, racemic form, their salt thereof according to claim 1, wherein X is a nitrogen atom, a sulfur atom, or a carbon atom.

5. The compound, racemic form, or salt thereof according to claim 4, wherein Y is an oxygen atom, or a nitrogen atom.

6. The compound, racemic form, or salt thereof according to claim 1, wherein $R^{1a}$ and $R^{1b}$ each independently represent a saturated or unsaturated aliphatic hydrocarbon group, an aromatic group, or a combination thereof.

7. A pharmaceutical composition comprising as an active ingredient the compound, racemic form, or salt thereof according to claim 1.

8. A method of treating a disease caused by a decrease of plasmalogen level within a living organism, comprising administering the pharmaceutical composition according to claim 7, wherein the disease is selected from the group consisting of cranial nerve disease, diabetes, metabolic syndrome, ischemic heart disease, insomnia, infection, and immune disorder.

9. The method according to claim 8, wherein the disease is cranial nerve disease, selected from dementia, Parkinson disease, depression, or schizophrenia.

10. The method according to claim 9, wherein the disease is dementia.

11. The method according to claim 10, wherein the dementia is Alzheimer-type dementia.

12. A compound presented by Chemical Formula 1, a racemic form, or a salt thereof:

[Chemical Formula 1]

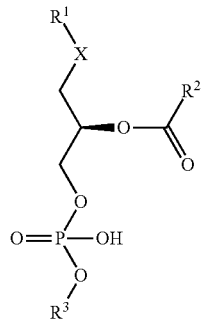
(I)

wherein,
X represents a nitrogen atom, a sulfur atom, or a carbon atom,
$R^1$ represents $R^{1a}$—Y—$R^{1b}$, wherein $R^{1a}$ and $R^{1b}$ each independently represent a saturated or an unsaturated aliphatic hydrocarbon group, an aromatic group, a heterocyclic group, or a combination thereof, Y represents an oxygen atom, a nitrogen atom, a sulfur atom, or a carbon atom,
$R^2$ represents a saturated or unsaturated aliphatic hydrocarbon group, and
$R^3$ represents choline, ethanolamine, inositol, or serine.

13. The compound, racemic form, or salt thereof according to claim 12, wherein Y is an oxygen atom, a nitrogen atom, or a sulfur atom.

14. The compound, racemic form, or salt thereof according to claim 12, wherein $R^{1a}$ and $R^{1b}$ each independently represent a saturated or unsaturated aliphatic hydrocarbon group, an aromatic group, or a combination thereof.

15. A pharmaceutical composition comprising as an active ingredient the compound, racemic form, or salt thereof according to claim 12.

16. A method of treating a disease caused by a decrease of plasmalogen level within a living organism, comprising administering the pharmaceutical composition according to claim 15, wherein the disease is selected from the group consisting of cranial nerve disease, diabetes, metabolic syndrome, ischemic heart disease, insomnia, infection, and immune disorder.

17. The method according to claim 16, wherein the disease is cranial nerve disease, selected from dementia, Parkinson disease, depression, or schizophrenia.

18. The method according to claim 16, wherein the disease is dementia.

19. The method according to claim 18, wherein the dementia is Alzheimer-type dementia.

* * * * *